US007384915B2

(12) United States Patent
Wang et al.

(10) Patent No.: US 7,384,915 B2
(45) Date of Patent: Jun. 10, 2008

(54) CHIMERIC INSULIN-GAD PROTEINS FOR TREATING PATIENTS WITH TYPE 1 DIABETES OR AT RISK OF DEVELOPING TYPE 1 DIABETES

(75) Inventors: Yi Wang, Orange, CT (US); John Mueller, Old Lyme, CT (US); Louis A. Matis, Southport, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 83 days.

(21) Appl. No.: 11/143,947

(22) Filed: Jun. 3, 2005

(65) Prior Publication Data

US 2006/0052581 A1    Mar. 9, 2006

Related U.S. Application Data

(60) Division of application No. 09/528,225, filed on Mar. 21, 2000, now Pat. No. 6,982,323, which is a continuation of application No. PCT/US98/27408, filed on Dec. 23, 1998.

(60) Provisional application No. 60/068,648, filed on Dec. 23, 1997.

(51) Int. Cl.
*C07K 14/62* (2006.01)
*C07K 14/435* (2006.01)
*A61K 38/17* (2006.01)
*A61K 38/28* (2006.01)
*A61K 38/43* (2006.01)

(52) U.S. Cl. ............................ 514/3; 514/866; 530/303; 530/350; 530/403; 536/234

(58) Field of Classification Search ........................ None
See application file for complete search history.

(56) References Cited

U.S. PATENT DOCUMENTS

| 4,431,740 A | 2/1984 | Graeme et al. |
| 4,939,094 A | 7/1990 | Kuga et al. |
| 5,691,448 A | 11/1997 | Baekkeskov et al. |
| 5,821,334 A | 10/1998 | Powers |
| 5,998,584 A | 12/1999 | Baekkeskov et al. |

FOREIGN PATENT DOCUMENTS

EP      0940470      9/1999

WO      WO-96/26218     8/1996

OTHER PUBLICATIONS

Abbas et al. Cell Mol. Immunol., 376-392. (1994).
Abo, S. et al. "Preparation of Highly Purified Human Myelin Oligodendrocyte Glycoprotein in Quantities Sufficient for Encephalitogenicity and Immunogenicity Studies." Bio. Molec. Biol. Int., 30:945-958. (1993).
Adorini, L. et al. "Selective Immunosuppression." Immunol. Today, 14:285-289. (1993).
Allegretta, M. et al. "Homologies Between T Cell Receptor Junctional Sequences Unique to Multiple Sclerosis and T Cells Mediating Experimental Allergic Encephalomyelitis." (1994).
Allegretta, M. et al. "T Cells Responsive to Myelin basic Protein in Patients with Multiple Sclerosis." Science, 247:718-722. (1990).
Alvord, E. et al. "Has Myelin Basic Protein Received a Fair Trial in the Treatment of Multiple Sclerosis?" Ann. Neurol., 6:461-468. (1979).
Ammerer. Meth. Enzymol. 101:192. (1983).
Amor, S. et al. "Identification of Epitopes of Myelin Oligodendrocyte Glycoprotein for the Induction of Experimental Allergic Encephalomyelitis in SJL and Biozzi AB/H Mice." Journal of Immunology, 153:4349-4356. (1994).
Aruga, J. et al. "Identification of the New Isoforms of Mouse Myelin Basic Protein: The Existence of Exon 5a."J. Neurochem, 56:1222-1226. (1991).
Atkinson and Maclaren. J. Clin. Invest. 92:1608-1616. (1993).
Atkinson et al. Diabetes, 39:933-937. (1990).
Atkinson et al. J. Clin. Invest. 91:350-356. (1993).
Atkinson et al. Lancet 335:1357-1360. (1990).
Atkinson et al. Lancet, 339:458-459. (1992).
Ausubel et al. Current Protocols in Molecular Biology, John Wiley & Sons, New York. (1994).

(Continued)

*Primary Examiner*—Christine J. Saoud
(74) *Attorney, Agent, or Firm*—Ropes and Gray LLP

(57)    ABSTRACT

Novel chimeric fusion proteins comprising immunodominant epitopes of GAD and insulin are provided. Also provided are immunomodulatory methods for the use of such proteins for both the prevention and treatment of Type 1 diabetes mellitus. The chimeric fusion proteins of the invention are useful in predicting risk of onset of Type I diabetes, determining prognosis of Type 1 diabetes patients early in disease progression, and in evaluating patients for suitability as recipients of transplants of pancreatic cells or tissues. The administration of the proteins of the invention in accordance with the immunomodulatory methods of the invention results in beneficial effects on disease development and severity in patients suffering from or predicted to be at risk of developing Type 1 diabetes, as well as on the outcome of transplants of pancreatic cells or tissues in Type I diabetes patients.

16 Claims, 9 Drawing Sheets

OTHER PUBLICATIONS

Baekkeskov et al. J. Clin. Invest. 79:926-934. (1987).
Baekkeskov et al. Nature 347:151-156. (1990).
Baekkeskov et al. Nature, 298:167-169. (1982).
Barnett, L. et al. "Enhancement of Autoimmune Disease Using Recombinant Vaccinia Virus Encoding Myelin Proteolipid Protein." J. Neuroimmunol., 44:15-26. (1993).
Bishopp, F. "Autoimmune Stock Sinks on Disappointing Phase III Myloral Trial Data in MS." Bioworld Today, 8(77):1. (1997).
Bock et al. Lancet, 339:1504-1506. (1992).
Boehme and Leardo. Eur. J. Immunol. 23:1552-1560. (1993).
Boehme, S. et al. "Propriocidal Apoptosis of Mature T Lymphocytes Occurs at S Phase of the Cell Cycle." Eur. J. Immunol., 23:1552-1560. (1993).
Bonifacio et al. Lancet, 335:147-149. (1990).
Bowman et al. Immunol. Today 15(3):115-120. (1994).
Brunner et al. Nature, 373:441-444. (1995).
Butler et al. J. Exp. Med. 178:2097-2106. (1993).
Carnegie, P. et al. "Amino Acid Sequence of the Encephalitogenic Basic Protein." Biochem. J., 123:57-67. (1971).
Chang et al. Nature, 275:615 et seq. (1978).
Chen, Y. et al. "Regulatory T Cell Clones Induced by Oral Tolerance: Suppression of Autoimmune Encephalomyelitis." Science, 265:1237-1240. (1994).
Chiang, B. et al. "Prospects of Vaccination in Autoimmune Diseases." Int. Arch. Allergy Immunol., 98:181-188. (1992).
Chou and Fasman. Adv. Enzymol. 47:45-147. (1978).
Chou, Y. et al. "Frequency of T Cells Specific for Myelin Basic Protein and Myelin Proteolipid Protein in Blood and Cerebrospinal Fluid in Multiple Sclerosis." J. Neuroimmunol., 38:105-114. (1992).
Chou, Y. et al. "Specificity of Human T Cell Clones Reactive to Immunodominant Epitopes of Myelin Basic Protein." J. Neurosci. Res., 28:280-290. (1991).
Chou. "Prediction of Protein Structure and the Principles of Protein Conformation." Plenum Press, pp. 549-586. (1990).
Cohen et al. Ann Rev. Immunol. 10:267 et seq. (1992).
Coligen et al. Current Protocols in Immunology, John Wiley & Sons, NY. (1995).
Conrad et al. Nature, 371:351-355. (1994).
Correale, J. et al. "Patterns of Cytokine Secretion by Autoreactive Proteolipid Protein-Specific T Cell Clones During the Course of Multiple Sclerosis." J. Immunology, 154:2959-2968. (1995).
Cotter et al. Anticancer Research, 10:1153 et seq. (1990).
Crispe. Immunity, 1:347-349. (1994).
Critchfield, J. et al. "T Cell Deletion in High Antigen Dose Therapy of Autoimmune Encephalomyelitis." Science, 263:1139-1143. (1994).
Daniel et al. Proc. Natl. Acad. Sci. USA, 93:956-960. (1996).
Davis et al. Basic Methods in Molecular Biology, 2nd ed., Appleton and Large, Norwalk, CT. (1995).
De Aizpurua et al. Proc. Natl. Acad. Science USA, 89:9841-9845. (1992).
Dhein et al. Nature, 373:438-441. (1995).
Diehl, H. et al. "Individual exons encode the integral membrane domains of human myelin proteolipid protein." Proc. Natl. Acad. Sci. USA, 83:9807-9811. (1986).
Duvall et al. Immunol. Today, 7:115-119. (1986).
Einstein et al. "The isolation from bovine spinal cord of a homogeneous protein with Encephalitgenic Activities." Neurochem. 9:252-361. (1962).
Elliott et al. J. Clin. Invest., 98:1-11. (1996).
Endoh, M. et al. "DM-20, A Proteolipid Apoprotein, Is an Ecephalitogen of Acute and Relapsing Autoimmune Encephalomyelitis in Mice." J. Immunol., 137:3832-3835. (1986).
Evans and Scarpulla. Gene, 84:135 et seq. (1989).
Falorni et al. Diabetologia, 39:1091-1098. (1996).
Farrell, Jr. RNA Methodolgies: A Laboratory Guide for Isolation and Characterization. Academic Press Inc., San Diego, CA. (1993).
Foster. Harrison's Principles of Int. Med, 13th Ed., McGraw-Hill, NY. pp. 1979-2000. (1994).
Fritz, R. et al. "Encephalitogenicity of Myelin Basic Protein Exon-2 Peptide in Mice." J. Neuroimmunol., 51:1-6. (1994).

Garnier et al. J. Mol. Biol, 120:97-120. (1978).
Goeddel et al. Nucl. Acids Res., 8:4057 et seq. (1980).
Greer, J. et al. "Identification and Characterization of a Second Encephalitogenic Determinant of Myelin Proteolipid Protein (Residues 178-191) for SJL Mice." J. Immunol., 149:783-788. (1992).
Griffin and Griffin. PCR Technology, Current Innovations, CRC Press, Boca Raton, FL. (1994).
Griffin et al. Am. J. Pathol., 147:845-857. (1995).
Grima, B. et al. "A Novel Transcript Overlapping the Myelin Basic Protein Gene." J. Neurochem., 59:2318-2323. (1992).
Grosjean and Fiers. Gene, 18:199 et seq. (1982).
Hanninen et al. J. Clin. Invest., 90:1901-1910. (1992).
Harrison. Immunol. Today, 13:348-352. (1992).
Harwood, Ed. Protocols for Gene Analysis: Methods in Molecular Biology, vol. 31, The Humana Press, Totowa, NJ. (1994).
Hatfield et al. Diabetologia, 40:1327-1333. (1997).
Hernan, R. et al. "Human Hemoglobin Expression in *Escherichia coli*: Importance of Optimal Codon Usage." Biochemistry, 31:8619-8628. (1992).
Herold et al. J. Exp. Med., 176:1107-1114. (1992).
Higgins, Paul et al. "Suppression of Experimental Autoimmune Encephalomyelitis by Oral Administration of Myelin Basic Protein and its Fragments." J. Immunol., 140:440-445. (1988).
Ho et al. Gene, 77:51-59. (1989).
Honeyman et al. J. Exp. Med. 177:353-340. (1993).
Horvath, L. et al. "Influence of Polar residue Deletions of Lipid-Protein Interactions with the Myelin Proteolipid Protien. Spin-Label ESR Studies with DM-20/Lipid Recombinants." Biochemistry, 29:2635-2638. (1990).
Huang and Gorman. Mol. Cell Biol., 10:1805 et seq. (1990).
Johnson, D. et al. "Cell-Mediated Immunity to Myelin-Associated Glycoprotein, Proteolipid Protein, and Myelin Basic Protein in Multiple Sclerosis." J. Neuroimmunol., 13:99-108. (1986).
Ju et al. Nature, 373:444-448. (1995).
Kamholz, J. "Organization and Expression of the Human Myelin Basic Protein Gene." J. Neurosci. Res., 21:62-70. (1988).
Kamholz, J. et al. "Identification of three forms of human myelin basic protein by cDNA cloning." Proc. Natl. Acad. Sci. USA, 83:4962-4966. (1986).
Karjalainen et al. New Eng. J. Med., 327:302-307. (1992).
Karounos and Thomas. Nature, 39:1085-1090. (1990).
Kaufman et al. J. Clin. Invest. 98:283-292. (1992).
Kaufman, D. et al. "Spontaneous Loss of T-Cell Tolerance to Glutamic Acid Decarboxylase in Murine Insulin-Dependent Diabetes." Nature, 366:69-72. (1993).
Kawabe and Ochi. Nature, 349:245-248. (1991).
Kawaskai et al. J. Clin. Endocrinol. Metab., 82:375-380. (1997).
Kennedy, M. et al. "Inhibition of Murine Relapsing Experimental Autoimmune Encephalomyelitis by Immune Tolerance to Proteolipid Protein and its Encephalitogenic Peptides." J. Immunol., 144:909-915. (1990).
Kerlero de Rosbo et al. "Reactivity to Myelin Antigens in Multiple Sclereosis." J. Clin. Invest., 92:2602-2608. (1993).
Kerr et al. Apoptosis: The Molecular Basis of Cell Death, Tomei and Cope (eds.), Cold Spring Laboratory Press, Plainview, NY, pp. 5 et seq. (1991).
Kim et al. Immunol. Invest., 22(3):219-227. (1993).
Klaus. Lymphocytes: A Practical Approach, IRL Press Oxford England. (1987).
Kronquist et al. "Expression of Myelin Proteins in the Developing Human Spinal Cord: Cloning and Sequencing of Human Proteolipid Protein cDNA." J. Neurosci., Res., 18:395-401. (1987).
Lehmann, P. et al. "Spreading of T-Cell Autoimmunity to Cryptic Determinants of an Autoantigen." Nature, 358:155-157. (1992).
Lenardo. Nature, 353:858-860. (1991).
Liblau, R. et al. "T-Cell Response to Myelin Basic Protein Epitopes in Multiple Sclerosis Patients and Healthy Subjects." Eur. J. Immunol., 21:1391-1395. (1991).
Lockshin and Zekeri. "Apoptosis: The Molecular Basis of Cell Death, Tomei and Cope (eds.)."Cold Spring Harbor Laboratory Press, Planview, NY. pp. 47-60. (1991).
Lohman et al. Horomone & Metabolic Res., 28:357-360. (1996).
Lohman et al. Lancet, 343:1607-1608. (1994).

Luckow et al. Bio/Technology, 6:47 et seq. (1988).
MacLaren, N. and K. Laffety. Diabetes, 42:1099-1104. (1993).
Maniatis. Molecular Cloning: A Laboratory Manual. (1982).
Marrack and Kappler. Science, 238:1073 et seq. (1987).
Martin, R. et al. "Diversity in Fine Specificity and T-Cell Receptor Usage of the Human CD4+ Cytotoxic T-Cell Response Specific for the Immunodominant Myelin Basic Protein Peptide 87-106." J. Immunol., 148:1359-1366. (1992).
Martin, R. et al. "Immunological Aspects of Demyelinating Diseases." Ann. Rev. Immunol., 10:153-187. (1992).
McRae, B. et al. "Induction of Active and Adoptive Relapsing Experimental Autoimmune Encephalomyelitis (EAE) Using an Encephalitogenic Epitope of Proteolipid Protein." J. Neuroimmunol., 38:229-240 (1992).
Meinl, et al. "Myelin Basic Protein-Specific T Lymphocyte Repertoire in Multiple Sclerosis." J. Clin. Invest, 92:2633-2643. (1993).
Miller, A. "Suppressor T Cells generated by oral tolerization to myelin basic protein suppress both in vitro and in vivo immune responses by the release of transforming growth factor after antigen-specific triggering." Proc. Natl. Acad. Sci. USA, 89:421-425. (1992).
Miller, A. et al. "Active suppression Versus Clonal Anergy Following Oral or IV Administration of MBP in Actively and Passively Induced EAE." Neurology, 42(suppl 3):301 et seq. (1992).
Miller, A. et al. "Suppression of Experimental Autoimmune Encephalomyelitis by Oral Administration of Myelin Basic Protein V. Hierarchy of Suppression by Myelin Basic Protein from Different Species." J. Neuroimmunol., 39:243-250. (1992).
Miller, S. et al. "The Immunopathogenesis and Regulation of T-Cell-Mediated Demyelinating Diseases." Immunol. Today, 15:356-361. (1994).
Mitchison. "Induction of Immunological Paralysis in Two Zones of Dosage." Proc. R. Soc. London, Ser B 161:275-280. (1964).
Moir et al. Meth. Enzymol, 194:491-507. (1991).
Morgenstern and Land. Nucl. Acids Res., 18:3587 et seq. (1990).
Muir et al. J. Clin. Invest., 95:628-634. (1995).
Mullins et al. Eds. The Polymerase Chain Reaction Springer. Verlag, New York, NY. pp. 263-273. (1994).
Nagata and Suba. Immunol. Today, 16:39 et seq. (1995).
Naquet et al. J. Immunol., 140:2569-2578. (1988).
Nossal et al. Diabetologia, pp. 549-559. (1992).
Oettinger, H. et al. "Biological Activity of Recombinant Human Myelin Basic Protein." J. Neuroimmunol., 44:157-162. (1993).
Ormerod, Ed. Flow Cytometry: A Practical Approach, 2nd ed. IRL Press at Oxford University Press Oxford England. (1994).
Paul. Fundamental Immunology 2nd ed., Raven Press, NY. (1989).
Pelfrey et al. "Identification of a Second T Cell Epitope of Human Proteolipid Protein (residues 89-106) recognized by proliferative and Cytolytic CD4+ T Cells from Multiple Sclereosis Patients," J. Neuroimmunol. 53:153-161. (1994).
Pelfrey et al. "Identification of Novel T Cell Epitope of Human Proteolipid (residues 40-60) Recognized by Proliferative and Cytolytic CD4+ T cells from Multiple Sclereosis Patients." J. Neuroimmunol. 46-33-42. (1993).
Pelfry et al. "Identification of a second T cell epitope of human proteolipid protein (residues 89-106) recognized by proliferative and cytolytic CD4+ t cells from multiple sclereosis patients." J. Neuroimmunol., 53:153-161. (1994).
Pereyra, P. et al. "Triton X-100 Extractions of Central Nervous System Myelin Indicate a Possible Role for the Minor Myelin Proteins in the Stability of Lamellae." Neurochem. Res., 13:583-595. (1988).
Pette, M. et al. "Myelin Basic Protein-Specific T Lymphocyte Lines from MS Patients and Healthy Individuals." Neurology, 40:1770. (1990).
Pham-Dinh, D. et al. "Characterization and Expression of the cDNA Coding for the Human Myelin/Oligodendrocyte Glycoprotein." J. Neurochem., 63:2353-2356. (1994).
Popot, J. et al. "Major Myelin Proteolipid: The 4 Alpha-Helix Topology." J. Memb. Biol., 120:233-246. (1991).
Proost, P. et al. "Leukocyte Gelatinase B Cleavage Releases Encephalitogens from Human Myelin Basic Protein." Bioch. Biophys. Res. Com., 192:1175-1181. (1993).
Qin, Y. et al. "Resistance to Experimental Autoimmune Encephalomyelitis Induced by Neonatal Tolerization to Myelin Basic Protein: Clonal Elimination vs. Regulation of Autoaggressive Lymphocytes." Eur. J. Immunol., 19:373-380. (1989).
Quinn, A. and E. E. Sercarz. J. Autoimmunity, 9:365-370. (1996).
Racke, M. et al. "Retinoid Treatment of Experimental Allergic Encephalomyelitis—IL-4 Production Correlates with Improved Disease Course," J. Immunol, 154:450-458. (1995).
Raine, C. Handbook of Clinical Neurology, 3(47:429-466, Koetsier (ed) Elsevier Science Publishers. (1985).
Ramiya et al. J. "Immunization Therapies in the Prevention of Diabetes." Journal of Autoimmunity, 10:287-292. (1997).
Ramiya et al. J. Autoimmunity, 9:349-356. (1996).
Remington's Pharmaceutical Science, Mack Publishing Co., Philadelphia, PA, 17th ed. (1985).
Richert, J. et al. "Evidence for multiple human T cell recognition sites on myelin basic protein." J. Neuroimmunol., 23:55-66. (1989).
Richter et al. Proc. Natl. Acad. Sci. USA, 89:8467-8471. (1992).
Roth, H. J. et al. "Evidence for the Expression of Four Myelin Basic Protein Variants in the Developing Human Spinal Cord Through cDNA Cloning." J. Neurosci. Res. 17:321-328. (1987).
Rudy et al. Mol. Medicine, 1:625-633. (1995).
Russell et al. Proc. Natl. Acad. Sci. USA, 90:4409-4413. (1993).
Saeki, Y. et al. "Transfer of Multiple Sclerosis into Severe Combined Immunodeficiency Mice by Mononuclear Cells from Cerebrospinal Fluid of the Patients." Proc. Natl. Acad. Sci. USA, 89:6157-6161. (1992).
Sakai et al. "Prevention of experimental encephalomyelitis with peptides that block interaction of T cells with major histocompatibility complex proteins." Proc. Natl. Acad. Sci., 86:9470-9474. (1989).
Salvetti, M. et al. "Predominant and Stable T Cell Responses to Regions of Myelin Basic Protein Can Be Detected in Individual Patients with Multiple Sclerosis." Eur. J. Immunol., 23:1232-1239. (1993).
Sambrook et al. Molecular Cloning: A Laboratory Manual, Cold Spring Harbor Press, Cold Spring Harbor, NY. (1990).
Sato et al. J. Biol. Chem, 269:17267 et seq. (1994).
Schena et al. Meth. Enzymol., 194:389-398. (1991).
Schwartz. Immunology 3rd ed., Raven Press, New York, pp. 1033-1097. (1993).
Segal et al. "Experimental Allergic Encephalomyelitis Induced by the Peptide Encoded by Exon 2 of the MBP Gene, A Peptide Implicated in Remyelination." J. Neuroimmunol., 51:7-19. (1994).
Segal et al. "Experimental Allergic Encephalomyelitis Induced by the Peptide Encoded By Exon 2 of the MBP Gene, A Peptide Implicated Remyelination." Neuroimmunol. 51:7-19. (1994).
Sercarz et al, "Specific Inhibition of Antibody Formation During Immunological Paralysis and Unresponsiveness." Nature 184:1080-1082. (1959).
Shpaer, E. "Constraints on Codon Context in *Escherichia coli* Genes, Their Possible Rode in Modulating the Efficiency of Translation." J. Mol. Biol., 188:555-564. (1986).
Singer et al. Immunity, 1:365-371. (1994).
Smith et al. "Antibodies to CD3/T-cell receptor Complex Induced Death by Apoptosis in Immature T Cells in Thymic Culture." Nature 337:181-184. (Jan. 12, 1989).
Sobel, R. et al. "Minireview: Autoimmune Responses to Myelin Proteolipid Protein." Neurochem. Res., 19:915-921. (1994).
Solimena and De Camilli. Nature, 366:15-17. (1993).
Sriram, S. et al. "Administration of Myelin Basic Protein-Coupled Spleen Cells Prevents Experimental Allergic Encephalitis." Cell Immunol., 75:378-382. (1983).
Steinnman. Cell, 80:7-10. (1995).
Strasser. Nature, 373:385-386. (1995).
Streicher and Stoffel. "The Organization of The Human Myelin Basic Protein Gene, Comparison with the Mouse Gene." Biol. Ghem Hoppe-Seyler 370:503-510. (1989).
Su, X. et al. "Treatment of Chronic Relapsing Experimental Allergic Encephalomyelitis with the Intravenous Administration of Splenocytes Coupled to Encephalitogenic Peptide 91-103 of Myelin Basic Protein." J. Neuroimmunol. 34:181-190. (1991).
Sun et al. Eur. J. Immunol. 21:1461-1468. (1991).
Taguchi et al. J. Immunol. Meth., 128:65-73. (1990).
Talib et al. Gene, 98:289-293, (1991).

Tisch et al. Nature, 366:72-75. (1993).

Traugott, U. et al. "Chronic Relapsing Experimental Autoimmune Encephalomyelitis, Treatment with Combinations of Myelin Components Promotes Clinical and Structural Recovery." J. Neurol. Sci, 56:65-73. (1982).

Tuohy, V. et al. "Myelin Proteolipid Protein: Minimum Sequence Requirements for Active Induction of Autoimmune Encephalomyelitis in SWR/J and SJL/Mice." J. Neuroimmunol., 39:67-74. (1992).

Tuohy, V. et al. "Peptide Determinants of Myelin Proteolipid Protein (PLP) in Autoimmune Demyelinating Disease: A Review." Neurochemical Research, 19:935-944. (1994).

Utz, U. et al. "Heterogeneity of T-Cell Receptor—Chain Complementarity-Determining Region 3 in Myelin Basic Protein-Specific T Cells Increases with Severity of Multiple Sclerosis." Proc. Natl. Acad. Sci. USA, 91:5567-5571. (1994).

Van Der Veen, R. "The Development and Characterization of Encephalitogenic Cloned T Cells Specific for Myelin Proteolipid Protein." J. Neuroimmunol., 26:139-145. (1990).

Van Der Veen, R. et al. "Immune Processing of Proteolipid Protein by Subsets of Antigen-Presenting Spleen Cells." J. Neuroimmunol., 38:139-146. (1992).

Van Noort, J. et al. "Fractionation of Central Nervous System Myelin Proteins by Reversed-Phase High-Performance Liquid Chromatography." J. Chromatogr. B 653:155-161. (1994).

Vandenbark, A. et al. "Immunization with a Synthetic T-Cell Receptor V-Region Peptide Protects Against Experimental Autoimmune Encephalomyelitis." Nature, 341:541-544. (1989).

Von Boehmer. Ann. Rev. Immunol., 6:309 et seq. (1988).

Voskuhl, R. et al. "A Novel Candidate Autoantigen in a Multiplex Family with Multiple Sclerosis: Prevalence of T-Lymphocytes Specific for an MBP Epitope Unique to Myelination." J. Neuroimmunol., 46:137-144. (1993).

Voskuhl, R. et al. "HLA Restriction and TCR Usage of T Lymphocytes Specific for a Novel Candidate Autoantigen, X2 MBP, In Multiple Sclerosis." J. Immunol., 153:4834-4844. (1994).

Voskuhl, R. et al. "T-Lymphocyte Recognition of a Portion of Myelin Basic Protein Encoded by an Exon Expressed During Myelination." J. Neuroimmunol 42:182-192. (1993).

Voskuhl, R. "T-Lymphocyte Recognition of a Portion of Myelin Basic Protein Encoded by an Exon Expressed During Myellnation." J. Neuroimmunol., 42:187-192. (1993).

Wada, K. et al. "Codon Usage Tabulated from the Genbank Genetic Sequence Data." Nucl. Acids. Res., 20:(Supplement) 2111-2118. (1992).

Walter et al. J. Clin. Invest., 8:163-166. (1994).

Waslston et al. N. Eng. J. Med., 333:343-347. (1995).

Wauben, M. et al. "Inhibition of Experimental Autoimmune Encephalomyelitis by MHC Class II Binding Competitor Peptides Depends on the Relative MHC Binding Affinity of the Disease-Inducing Peptide." J. Immunol., 150:4211-4220. (1994).

Weimbs, T. et al. "Proteolipid Protein (PLP) of CNS Myelin: Positions of Free, Disulfide-Bonded, and Fatty Acid Thioester-Linked Cysteine Residues and Implications for the Membrane Topology of PLP." Biochemistry, 31:12289-12296. (1992).

Weiner, H. et al. "Double-Blind Pilot Trial of Oral Tolerization with Myelin Antigens in Multiple Sclerosis." Science, 259:1321-1324. (1993).

Weir. Handbook of Experimental Immunology 3rd ed., vol. 2, Cellular Immunology Blackwell Scientific Publication, Oxford, Engand. (1978).

Wen et al. "Induction of Insulitis by Glutamic Acid Decarboxylase Peptide-Specific and HLA-DQ8-restricted CD4 T Cells from Human DQ Transgenic Mice." J. Clin. Invest 102(5):947-957. (Sep. 5, 1998).

Whitham, R. et al. "Location of a New Encephalitogenic Epitope (Residues 43 to 64) in Proteolipid Protein that Induces Relapsing Experimental Autoimmune Encephalomyelitis in PL/J and (SJL X PL) F1 Mice." J. Immunol., 147:3803-3808. (1991).

Whitham, R. et al., "Lymphocytes from SJL/J Mice Immunized with Spinal Cord Respond Selectively to a Peptide of Proteolipid Protein and Transfer Relapsing Demyelinating Experimental Autoimmune Encephalomyelitis." J. Immunol., 147:101-107. (1991).

Whitman, R. et al. "Lymphocytes from SJL/J Mice Immunized with Spinal Cord Respond Selectivity to a Peptide of Proteolipid Protein and Transfer Relapsing Demyelinating Experimental Autoimmune Encephalomyelitis." J. Immunol. 146:101-107. (1991).

Wicker et al. J. Clin. Invest., 98:2597-2603. (1996).

Williams et al. Nuc. Acids Res., 16:10453 et seq. (1988).

Williams, D. et al. "Design, Synthesis and Expression of a Human Interleukin-2 Gene Incorporating the Codon Usage Bias Found in Highly Expressed *Escherichia coli* Genes." Nucl. Acids Res., 16:10453-10467. (1988).

Wong et al. J. Clin. Invest., 102:947-957. (1998).

Wucherpfenning, K. et al. "Clonal Expansion and Persistence of Human C Cells Specific for an Immunodominant Myelin Basic Protein Peptide." J. Immunol., 152:5581-5592. (1994).

Xie et al. J. Immunol., 159:3662-3667. (1997).

Yoon. "MS Study Yields Mixed Results." Science, 259:1263. (1993).

Zamvil et al. "T cell epitope of the autoantigen myelin basic protein that induces encephalomyelitis." Nature, 324:258-260. (1986).

Zhang et al. Diabetes, 46:40-43. (1997).

Zhang et al. Proc. Natl. Acad. Sci. USA, 88:10252-10256. (1991).

Zhang, J. "MHC-Restricted Depletion of Human Myelin Basic Protein-Reactive T Cells by T Cell Vaccination." Science, 261:1451-1454. (1993).

Zhang, J. "Myelin Basic Protein-Specific T Lymphocytes in Multiple Sclerosis and Controls: Precursor Frequency, Fine specificity, and Cytotoxicity." Ann. Neurol., 32:330-338. (1992).

Zhang, J. et al. "Increased Frequency of Interleukin 2-responsive T Cells Specific for Myelin Basic Protein and Proteolipid Protein in Peripheral Blood and Cerebrospinal fluid of Patients with Multiple Sclerosis." J. Exp. Med., 179:973-984. (1984).

IG1

IG2

IG3

☐ Insulin B
■ Insulin C
▦ hGAD65/115-127
▨ hGAD65/247-286
▥ hGAD65/473-5--

IG4

☐ Insulin B chain (aa 1-31)
■ Insulin C Peptide (aa 32-67)
▩ hGAD65/202-236-GGG (aa68-105)
▦ hGAD65/115-127 (aa 106-118)
▨ hGAD65/247-300 (aa 119-175, GGG at aa 146-148)

IG6

- ☐ Insulin B chain (aa 1-31)
- ■ Insulin C Peptide (aa 32-67)
- ▨ hGAD65/202-236-GGG (aa68-105)
- ▦ hGAD65/115-127 (aa 106-118)
- ░ hGAD65/247-300 (aa 119-175, GGG at aa 146-148)
- ▩ GGG-hIA2/771-979 (aa 176-387)

CHIMERIC INSULIN-GAD PROTEINS FOR TREATING PATIENTS WITH TYPE 1 DIABETES OR AT RISK OF DEVELOPING TYPE 1 DIABETES

CROSS REFERENCE TO RELATED APPLICATION

This application is a divisional of U.S. patent application Ser. No. 09/528,225, filed Mar. 21, 2000, now U.S. Pat. No. 6,982,323 which is a continuation of PCT Application No. PCT/US98/27408, filed Dec. 23, 1998, which claims the benefit of U.S. provisional application Ser. No. 60/068,648, filed Dec. 23, 1997, all of which is incorporated herein by reference.

BACKGROUND OF THE INVENTION

The discussion in this section is not limited to subject matter that qualifies as "prior art" against the present invention. Therefore, no admission of such prior art status shall be implied or inferred by reason of inclusion of particular subject matter in this discussion, and no declaration against the present inventors' interests shall be implied by reason of such inclusion.

Diabetes Mellitus

Diabetes mellitus is the most common endocrine disease, and is characterized by abnormalities of glucose metabolism. The abnormal glucose metabolism associated with this disease results in hyperglycemia (high blood glucose levels) and eventually causes complications of multiple organ systems, including eyes, kidneys, nerves, and blood vessels. Patients with persistent hyperglycemia or abnormal glucose tolerance are generally diagnosed with the disease, although most commonly patients initially present with excessive urination (polyuria) and frequent drinking due to extreme thirst (polydipsia). These typical initial symptoms result from the osmotic effects of hyperglycemia.

The pathogenesis of diabetes mellitus is typically associated with pancreatic dysfunction, particularly of the beta cells of the pancreatic islets of Langerhans. This dysfunction may lead to destruction of the islet beta cells, which produce insulin, a glucose regulatory peptide hormone. Diabetes mellitus has been generally categorized as insulin dependent or type 1, versus non-insulin dependent, or type 2. However, this terminology has evolved as the disease has become better understood. For example, it has been found that in some patients suffering from non-insulin dependent diabetes, the disease progresses into an insulin dependent form, while in other patients insulin dependence does not develop.

Patients are thus often categorized in terms of the mechanisms of pathogenesis of islet destruction, and the designation type 1 is now used to refer to autoimmune islet pathogenesis, i.e., to diabetes caused by islet-specific autoimmune attack, and is so used herein. The term insulin dependent diabetes mellitus (IDDM) refers to Type 1 diabetes that has progressed to a stage where enough autoimmune destruction of the pancreatic beta cells has occurred to produce overt symptoms. The term pre-IDDM refers to an autoimmune condition that can be detected by biopsy or by analysis of autoimmune responses, in which pancreatic islet beta cells are being subject to a specific autoimmune attack to an extent where some cells may be subject to destruction. In pre-IDDM, however, the destruction (if any) has not progressed to an extent sufficient to require the administration of insulin. Since there can be a point in the early stages of Type 1 diabetes in which overt symptoms are observed but some islet function remains (known as the "honeymoon period", not all Type 1 diabetes is classified as IDDM, and not all pre-IDDM presents without overt symptoms.

Complications of Type 1 Diabetes The metabolic complications associated with the abnormal metabolism caused by insulin insufficiency can affect numerous organ systems. The most common acute metabolic complication is that of diabetic ketoacidosis, characterized by severe hyperglycemia (and resulting hypovolemia caused by osmotic diuresis) as well as metabolic acidosis induced by excess free fatty acid release and the production of ketone bodies.

In addition to the acute metabolic complication of ketoacidosis, the diabetic patient is susceptible to a series of late complications that cause considerable morbidity and premature mortality. Atherosclerosis occurs more extensively and earlier in diabetics than in the general population as a result of abnormalities in both glucose and lipid metabolism. This vascular pathology can lead to, inter alia, coronary artery disease, stroke, and peripheral vascular disease with gangrene. Retinopathy is another vascular complication of diabetes. Diabetic retinopathy is a leading cause of blindness, and is initiated by increased permeability of retinal capillaries which can progress to occlusion, hemorrhage, aneurysm formation, and neovascularization known as proliferative retinopathy.

In addition to vascular complications, kidney and neurological diseases (nephropathies and neuropathies) are common complications of diabetes. Diabetic nephropathy causes about half of end-stage renal disease in the United States. Histologically, the nephropathy is characterized by glomerular basement membrane widening and mesangial thickening. Initial signs include increasing proteinuria, with azotemia ultimately leading to renal failure. Diabetic neuropathy can affect any part of the nervous system, with the possible exception of the brain. The neuropathy is most commonly seen as peripheral polyneuropathy, with symptoms including numbness, paresthesias, severe hyperesthesias, and pain. Autonomic neuropathy can cause gastrointestinal dysfunction, orthostatic hypotension, bladder dysfunction or paralysis, and impotence. Diabetic foot ulcers represent a special problem of diabetics, and appear to be due primarily to abnormal pressure distribution secondary to diabetic neuropathy. The ulcerous lesions are often worsened by concomitant peripheral vascular disease and infection.

As mentioned above, meticulous control of blood glucose has been associated with amelioration of the late complications of Type 1 diabetes, suggesting that that preservation or restoration of beta cell function could reduce or eliminate the majority of the pathologic complications of the disease.

Pathogenesis of Type 1 Diabetes Type 1 diabetes only develops in genetically susceptible individuals, and symptoms generally appear before age 40, with the peak incidence of onset of overt symptomology occurring in the second decade of life. The pathogenesis of Type 1 diabetes is characterized by an initial phase of leukocyte infiltration into the islets, referred to as insulitis, followed over a period of time by the actual destruction of the islet beta cells by autoimmune attack. The insulitis phase is characterized by infiltration of pancreatic islets by both lymphocytes and cells of the monocyte/macrophage lineage, and entails both cell-mediated inflammation as well as attack by islet-specific cytotoxic antibodies. Overt clinical symptoms of diabetes mellitus are generally manifested when over 90% of the islet beta cells are destroyed; however, as discussed more fully below, it is now possible to accurately detect individuals undergoing earlier stages of type 1 pathogenesis, i.e., before enough islet beta cells have been lost to produce overt clinical symptoms.

The autoimmune process is generally thought to be induced by an environmental stimulus. One reason for this belief is that an identical twin has only a fifty/fifty chance of developing IDDM if his identical sibling has the disease.

T Cells The autoimmune destruction of the beta cells of the pancreatic islets in Type 1 diabetes is believed to be initiated by white blood cells (leukocytes), most importantly T cells. T cells, or T-lymphocytes, are mononuclear white blood cells that provide many essential immune functions. The importance of T cells in human autoimmune diseases has been increasingly appreciated in the past two decades. Studies using treatments that result in generalized immunosuppression have defined a critical role for a subset of T cells, known as CD4+ or helper T cells, as primary regulators of all immune responses (both cellular and humoral) to protein or peptide antigens.

T cells mediate tissue injury by indirect and direct means. T cells of both $CD8^+$ (cytotoxic) and $CD4^+$ (helper) subsets secrete a variety of inflammatory cytokines that can damage tissues indirectly by activating various other types of white blood cells. Examples of such T cell effects include activation of antibody secreting B cells (stimulating humoral immune activity) and activation of macrophages, which can cause acute tissue damage and inflammation by releasing hydrolytic enzymes, reactive oxygen species, and additional pro-inflammatory cytokines. In addition to these indirect effects of T cell activity, direct tissue damage can be mediated by $CD8^+$ cytotoxic T cells attacking cells displaying target antigens.

One unique aspect of the physiology of T cells is the presence of membrane bound antibody-like binding structures called T cell receptors (TCRs) on their cell surfaces. Like antibodies, TCRs bind with high specificity to particular antigens. Like antibody-producing cells, which develop as multitudinous clones of cells, each clone producing antibodies with unique specificities, T cells develop as a vast number of distinct clones, and any particular T cell clone expresses a single type of TCR with a defined binding specificity. T cell clones with TCRs that bind specifically to self antigens are responsible for the development of autoimmune diseases.

Studies of the interactions of antibodies and TCRs with their specific antigens have shown that a particular polypeptide antigen typically comprises numerous submolecular features, known as epitopes, that each can serve as a distinct binding site for a particular antibody or TCR.

T Cells and Autoimmune Diseases In autoimmune diseases, only a 25 limited number of T cell clones, reactive with various epitopes of a small number of autoantigens, become activated and are involved in pathogenesis. Even in individuals suffering from autoimmune diseases, only a small percentage of T cell clones (0.1-1%) are known to recognize autoantigens.

Various mechanisms have been postulated to play a role in the pathogenic activation of disease-causing autoreactive T cells. Primary activation of antigen presenting cells (APCs) by infection or local inflammation is implicated in one such mechanism. APCs activated in this way can then provide powerful co-stimulation for hitherto unreactive T cells.

Other proposed mechanisms involve the polyclonal activation of previously quiescent autoreactive T cells by superantigens, such as bacterial toxins; or a coincidental molecular mimicry between foreign and self antigens (Abbas et. al. 1994). In this last case, the host immune system mounts a response to an epitope on a protein expressed by a pathogen, such as a virus, that resembles a homologous epitope on a host protein. Autoimmune attack then results from the cross-reactive immune response that ensues.

In addition to external factors, underlying the emergence of all T cell-mediated autoimmune disease is a complex pattern of inherited susceptibility determined by multigenic factors. For further discussions of these various factors, Steinman, 1995, reviews current theories of autoimmunity.

Alterations in the T cell repertoire occur naturally during T cell development. Only a small fraction of thymocytes (immature T cells) survive the intrathymic development and selection events that result in emigration of developing T cells to the peripheral circulation and the completion of their maturation (von Boehmer, 1988; Marrack and Kappler, 1987). Experimental evidence strongly suggests that a large number of thymocytes that bear receptors for autoantigens are initially present in the thymus. Recent studies have yielded evidence suggesting that a process referred to as programmed cell death, or apoptosis, destroys these autoreactive thymocytes in the thymus while sparing thymocytes that are not autoreactive. Apoptosis thus plays a large role in shaping and maintaining the T cell repertoire and contributes to the establishment of self-tolerance by actively eliminating cells expressing autoreactive TCRs.

It has recently been discovered that T cells are sensitive to apoptotic cell death induced by a variety of stimuli at multiple points in their lifespan (see, for example, Lenardo 1991; Boehme and Lenardo 1993; Critchfield et al. 1994). Positive selection factors are also believed to play a role in regulating the survival of specific T cell clones. The reduction or expansion of the number of individual T cells of a particular clone in an organism by these and other mechanisms serve to modulate the responsiveness of the organism's immune system to a particular antigen. It is now firmly established in several autoimmune disease models, as well as in certain viral infections, that apoptosis can be induced (upon exposure to antigen under certain defined conditions) in mature peripheral antigen-specific T lymphocytes as well as in immature thymocytes.

Apoptosis occurs in many biological systems (see, for example, Kerr et al. 1991; Lockshin and Zakeri, 1991; Cohen et al. 1992; Duvall and Wyllie, 1986; Cotter et al. 1990). A cell undergoing apoptosis undergoes a specific program of events—cellular and biochemical processes that depend upon active metabolism and contribute to the cell's self-destruction. In apoptotic T cells, the nucleus shrinks, the chromatin condenses, the genetic material (DNA) progressively degrades into small (nucleosomal repeat sized) fragments, there is cytoplasmic compaction, the cell membrane forms blebs, and the cell eventually collapses (Kawabe and Ochi, 1991; Smith et al. 1989). Cells cannot recover from apoptosis, it results in irreversible cell death (Kawabe and Ochi, 1991; Smith et al. 1989).

Recent reports have suggested a role for the TNF-related cytokine known as the FAS ligand and its receptor, CD95 (the FAS receptor), in the induction of apoptosis in T cells (Crispe et al. 1994; Nagata and Suda, 1995; Strasser, 1995; Dhein et al., 1995; Brunner et al., 1995; and Ju et al., 1995).

Islet Beta Cell Autoantigens As discussed above, the onset of Type 1 diabetes is considered to be mediated by T cells. The disease is believed to be a consequence of inappropriate T cell responses specific to certain islet beta cell proteins that act as autoantigens. In addition to autoreactive T cells, autoantibodies against various self antigens have also been reported in IDDM patients. The antigens reported to be bound by these autoantibodies include many of those that have been reported to be recognized by autoreactive T cells.

Autoantigens that are subject to autoimmune responses in Type 1 patients include the 64-65 kDa GAD (glutamate decarboxylase) and the 67 kDa GAD autoantigens; insulin;

sialyglycolipid; a 38 kD antigen from the secretory granules of beta cells; an antigen cross reactive with antibodies to bovine albumin known as the beta cell p69 protein, PM-1, or disease-modifying antigen, a beta cell cytoskeletal protein known as peripherin, glucose transporter proteins, including GLUT-2; heat shock protein 65 (HSP 65), including the p277 peptide; carboxypeptidase H; a 52 Kd molecular mimic of Rubella virus antigen; a beta cell membrane associated protein of 150 kDa; a protein antigen located at the secretory pole of the rat insulinoma cell line RINm38, referred to as the RIN polar antigen; and (at first) poorly characterized antigens isolated by immunoscreening of an islet cDNA expression library, referred to as ICA12 and ICA512. ICA512, now also known as IA-2, is immunologically related to phogrin, which is also subject to autoimmune responses in Type 1 patients (Hatfield et al., 1997).

The relative importance of these various autoantigens to autoimmune pathogenesis, and the timing with which each plays a role during the course of disease onset and development, are the subject of considerable uncertainty and consequent controversy in the art. Further uncertainty stems from the fact that each supposed autoantigen comprises numerous epitopes, some of which may be have disease promoting effects while others may have disease suppressive effects.

While not wishing to be bound by any particular theory of operation, in accordance with certain aspects of the invention insulin and GAD are believed to provide the most effective therapeutic effects on the development of Type 1 diabetes of any of the autoantigens implicated as playing a role in the pathogenesis of the disease. In accordance with certain other aspects of the invention, IA-2 is also believed to provide effective therapeutic effects.

Autoantibodies to 64-65 kD GAD (hereinafter GAD 65) normally are detected before the onset of clinical insulin dependent Type 1 diabetes mellitus, and among nondiabetic relatives of patients with IDDM as well as others at risk. These autoantibodies have been suggested to be the best predictive autoantibody marker for impending Type 1 diabetes.

GAD 65 and GAD 67 are encoded by different genes on different chromosomes, the genes being about 70% homologous. Human islets only express GAD 65, although both protein forms are found in the brain. Evidence of lymphocyte specific immunity to GAD 65 has been demonstrated and found to be closely associated with IDDM. Recent studies in the NOD mouse model of diabetes have indicated that T cell responses to GAD 65 precede those to other putative autoantigens and that early induction of T cell tolerance to GAD 65 can prevent onset of disease.

Kaufman et al (1993) and Tisch et al (1993) have presented data that suggest that GAD responses are the most important in disease development, as they were reported to arise first during the development of Type 1 diabetes, with responses to other beta cell autoantigens only appearing much later in the course of the disease, with insulin reactivity being amongst the last to appear. These findings were interpreted as indicating that GAD 65 is the key autoantigen in Type 1 diabetes, and that modulation of autoimmune reactivity with GAD would be the most appropriate target for reducing disease pathology. In accordance with this theoretical understanding of disease progression, modulation of insulin reactive T cells would be closing the barn door after the horses had gone, the anti-insulin reactions being observed so late in disease progression that their modulation would not be expected to affect the onset or severity of disease.

Insulin autoantibodies (IAA) can be detected in around 50% of new onset patients, and are highly associated with islet cell autoantibodies (ICA) and the HLA-DR4 phenotype. Other studies suggest that individuals with both ICA and IAA have a much higher risk for developing overt Type 1 diabetes than those with either marker alone. T cell responses to insulin as an autoantigen have also been described. In one study cellular responses to human insulin were present in almost 90% of ICA-positive first degree relatives of IDDM patients. Also, as discussed below in the examples, insulin reactive T cells from diabetic NOD mice can transfer diabetes to non-diabetic NOD mice.

Responses of T cells from Type 1 diabetes patients or from at-risk individuals to undefined islet cell preparations have suggested that T cells also respond to other islet cell antigens. These include a 38 kD antigen from the secretory granules of beta cells, and serum albumin. In addition, heat shock protein (HSP) 65 has been implicated as a T cell autoantigen based upon the finding that HSP-specific T cells transfer disease in NOD mice.

Carboxypeptidase H is a molecule found in islet secretory granules and is associated with the production of peptide hormones and neurotransmitters. It was identified as a potential islet autoantigen by the screening of cDNA expression libraries with sera from IDDM or pre-IDDM patients.

Several other putative islet cell antigens, such as ICA12 and ICA512, have also been identified by screening of cDNA expression libraries.

Intra-antigenic and inter-antigenic spread of autoreactivity ("epitope spreading") are related phenomena associated with autoimmune diseases in which additional epitopes within an antigen, or additional antigens within a target tissue, become targeted by autoreactive T cells during disease progression. Such antigen spreading has been observed during the course of the inflammatory autoimmune process in the murine models of experimental allergic encephalomyelitis (EAE) and insulin-dependent diabetes (Lehmann et al. 1992; McCarron et al. 1990; Kaufman et al. 1993; Tisch et al. 1993).

These findings of antigen/epitope spreading suggest that for a therapeutic treatment to provide effective immune tolerance to islet beta cell autoantigens, the treatment will need to target a heterogeneous population of specific autoreactive T cells. Therefore, in order for antigen administration to be maximally effective in the prevention and treatment of Type 1 diabetes, it is desirable that a plurality of the immunodominant epitopes of both insulin and GAD 65 be presented to the disease producing autoreactive T lymphocytes.

Prediction and Diagnosis of Type 1 Disease As discussed above, there is a genetic aspect to the incidence of Type 1 diabetes. Accordingly, genetic tests can identify certain individuals at increased risk of developing the disease (see, for example, Walston et al. 1995). Furthermore, individuals with a known family history of the disease can be monitored for early, preclinical signs of disease development, e.g., by monitoring levels of the autoantibodies and autoreactive T cells discussed herein.

Autoantibodies Among the autoantibodies known to be associated with Type 1 diabetes, those directed against GAD 65 are the ones that appear earliest and are present in the largest number of patients. Overall, recent studies have shown that over 80% of individuals with preclinical diabetes have GAD-specific autoantibodies. In this case an individual with preclinical disease is defined as a first degree relative of a Type 1 diabetes patient with ICA. The antigens identified by ICA are ill-defined, but together with IAA and GAD-specific autoantibodies, they yield a high predictive value for onset of diabetes in preclinical individuals. Interestingly, in actual early onset disease, the frequency of GAD-specific antibodies declines. This could be due to the fact that GAD 65 reactivity declines with beta cell destruction.

Prediction of Type 1 diabetes may also be facilitated by monitoring of the subject's blood sugar levels, preferably, in conjunction with the administration of a glucose tolerance test to the subject. Such procedures are preferably carried out in combination with the monitoring of titers of the subject's circulating IAA, ICA, and GAD autoantibodies.

In accordance with the present invention, the chimeric proteins of the invention are fusion proteins that may be used as antigenic substrates for the detection of circulating autoantibodies, particularly IAA and/or GAD 65 autoantibodies, in diagnostic assays such as Western blot, ELISA, RIA, ELISPOT, and the like.

T cells Assays for the detection of T cells with specific reactivities are well known in the art, and include the mixed lymphocyte reaction (MLR) and the ELISPOT assay. ELISPOT assays are described, for example in Taguchi et al., J Immunol Meth 1990, 128:65 and Sun et al., J Immunol 1991 146:1490. In accordance with the invention, the chimeric fusion proteins of the invention may be used as substrates in such assays for the detection and quantification of insulin reactive T cells and/or GAD 65 reactive T cells and/or IA-2 reactive T cells.

Current Methods for Prevention and Treatment of Type 1 Diabetes. While diabetes has been studied for centuries, only a few effective treatments are available for type 1 disease. The first line of treatment is diet, with appropriate caloric intake based on ideal body weight and a defined distribution among protein, glucose, and fat. However, in IDDM patients, the most important component of therapy is the administration of insulin, the goal of which is to maintain glucose levels as close to the normal range as possible throughout the day. Insulin is available in rapid, intermediate, and long-acting formulations which vary in onset, peak, and duration of action, and can be used in varying schedules of administration to attempt to optimally regulate plasma glucose levels.

Intensive insulin therapy refers to a rigorous regimen of administration of hormonally effective insulin and monitoring of blood sugar levels. This regimen is designed to control blood glucose as precisely as possible. The results of the multicenter Diabetes Control and Complication Trial established that complications of diabetes are significantly diminished by better control of blood glucose levels, and thus demonstrated the desirability of intensive insulin therapy. One problem with this approach is that intensive insulin therapy requires a high level of patient awareness and compliance, as well as a highly skilled care team of physicians, nurses, and dietitians. The goals of intensive insulin therapy are thus extremely difficult to achieve, even with motivated and educated patients. Another problem is that a higher rate of hypoglycemia is seen in such rigorously treated patients than in patients receiving standard, less rigorous, insulin regimens.

The Diabetes Control and Complication Trial highlighted not only the benefit to overall metabolic health of maintaining normal blood glucose levels, but also a fundamental problem associated with the treatment of Type 1 diabetes, namely that the overt symptoms of the disease are manifested only when essentially all of the patients' islets are destroyed. Oral agents for diabetes, such as the sulfonylureas, act primarily by stimulating the release of insulin from dysfunctional beta cells, and thus are not useful for most patients with type 1 disease, i.e. for those patients with IDDM.

A major goal in the treatment of diabetes has been to develop therapies capable of aborting the autoimmune attack on the islet beta cells prior to their complete destruction, thereby preserving enough endogenous function to maintain normal metabolic control.

Induction of tolerance In the NOD (non-obese diabetic) mouse model of diabetes, it has been shown that oral feeding of insulin delayed the onset and reduced the severity of the disease. The mechanism proposed to explain oral tolerance is that oral antigen administration induces populations of antigen-specific Th2 T cells that secrete antiinflammatory cytokines such as IL-4, IL-10, and TGF-beta. These T cells circulate and are activated to secrete cytokines only in the presence of their specific antigen. Thus, insulin-specific Th2 T cells would be activated only in the pancreas where they would produce suppressive cytokines to modulate the autoimmune process. This mechanism does not require, therefore, that the oral antigen actually represent a disease-specific autoantigen, but rather only that it is expressed in a tissue specific fashion.

In contrast, methods designed to produce T cell tolerance (e.g., by anergy or apoptosis) require the identification of the actual disease-specific autoantigens that are targeted by autoimmune attack. Such antigens are then administered to patients in an appropriate tolerizing fashion (which may also induce non-antigen-specific tolerizing effects). Given that Type 1 diabetes is in significant measure a disease mediated by islet-specific autoreactive T cells, therapy of this type should be feasible in principle. Thus, induction of neonatal tolerance to GAD 65, as referred to above, prevented onset of disease in NOD mice. In addition, injection of crude islet extracts intrathymically, where tolerization of developing T cells takes place, has also protected both NOD mice as well as pre-diabetic BB rats from developing clinical disease.

One approach taken to induce insulin tolerance involves the parenteral administration of insulin, in combination with a conventional adjuvant (e.g., Freund's adjuvant). Typically this approach involves the administration of doses of insulin that would not be large enough to be expected to cause insulin shock in the patient. Notably, the insulin moieties of the chimeric fusion proteins of the present invention are hormonally ineffective, and are thus suitable for use in accordance with the methods of U.S. application Ser. No. 08/565,769, filed in the name of Yi Wang, which is incorporated herein by reference.

Apoptosis Apoptosis is a form of programmed cell death that occurs in many biological systems (Kerr et al., 1991; Lockshin and Zakeri, 1991; Cohen et al., 1992; Duvall and Wyllie, 1986; Cotter et al., 1990). As discussed above, an apoptotic cell undergoes a specific program of events that depend upon active metabolism and contribute to its own self-destruction. T cells that do not undergo apoptosis, but which have become activated, will carry out their "effector" functions by causing cytolysis, or by secreting lymphokines that cause B cell responses or other immune effects (Paul, 1989, pp. 3-38). These "effector" functions are the cause of tissue damage in autoimmune and other diseases. A powerful approach to avoiding disease is thus to permanently eliminate by apoptosis only those T cells reactive with autoimmune disease-inciting antigens, while leaving the majority of the T cell repertoire intact. The use of auto-antigens to carry out this approach is described in PCT patent publication No. 94/28926, filed in the name of Michael J. Lenardo, and entitled Interleukin-2 Stimulated T Lymphocyte Cell Death for the Treatment of Autoimmune Diseases, Allergic Disorders, and Graft Rejection, and PCT patent publication No. 94/03202, filed in the name of Michael J. Lenardo, Stefen A. Boehme, and Jeffrey Critchfield and entitled Interleukin-4 Stimulated T Lymphocyte Cell Death, both of which patent publications are incorporated herein by reference.

Transplantation Transplantation of healthy pancreata, pancreatic tissue, or isolated pancreatic islets into patients suffering from Type 1 diabetes provides an effective treatment modality. Unfortunately, the duration of the therapeutic benefit of such transplants is currently limited by the same autoimmune phenomena that cause type 1 disease in the first place. Accordingly, treatment of a diabetic patient using the chimeric fusion proteins of the invention in accordance with the methods of the present invention, when carried out prior to, concomitantly with, and/or shortly after such a transplant, will increase the longevity of such transplants and thereby enhance the therapeutic benefit of such transplantation procedures.

The accompanying figures, which are incorporated in and constitute part of the specification, illustrate certain aspects of the invention, and together with the description, serve to explain the principles of the invention. It is to be understood, of course, that both the figures and the description are explanatory only and are not restrictive of the invention.

SUMMARY OF THE INVENTION

Figure 1A:
FIG. 1A shows a schematic diagram of the IG1 fusion protein (SEQ ID NO:1). The numbers following the slashes in the legend indicate the GAD 65 peptide moiety to which region corresponds. For hGAD 65/473-5--, 5-- indicates 555.
Figure 1B:
FIG. 1B shows a schematic diagram of the IG2 fusion protein (SEQ ID NO:2). The numbers following the slashes in the legend indicate the GAD 65 peptide moiety to which region corresponds. For hGAD 65/473-5--, 5-- indicates 555.
Figure 1C:
FIG. 1C shows a schematic diagram of the IG3 fusion protein (SEQ ID NO:3). The numbers following the slashes in the legend indicate the GAD 65 peptide moiety to which region corresponds. For hGAD 65/473-5--, 5-- indicates 519.

In view of the foregoing, the objects of this invention include the provision of novel chimeric fusion proteins that act as single molecular entities that 1) facilitate diagnosis and prognostic evaluation of individuals suspected of predisposition for the development of IDDM, as well as those suffering from IDDM and/or Stiff-Man syndrome, and 2) to provide enhanced beneficial effects when administered to animals (including human patients) suffering from or at risk of developing autoimmune (Type 1) diabetes. To these ends the invention provides chimeric fusion proteins comprising epitopes of both GAD (glutamate decarboxylase) and insulin. Preferably the GAD is GAD 65 and the GAD and insulin are human GAD and insulin.

In accordance with the invention, the combination of GAD 65 and insulin peptides in a single fusion protein provides a more convenient diagnostic reagent for the detection and prognostic evaluation of diabetes or stiff man syndrome. Discussion of Stiff-Man syndrome may be found, for example in U.S. Pat. No. 5,691,448, which is incorporated herein by reference.

In accordance with the invention, (and as set forth in the examples, below) the combination of GAD 65 and insulin chains and/or peptides in a single chimeric fusion protein further provides a compound which can be administered so as to furnish more effective immunomodulatory therapeutic treatment than the combination of the same peptides and/or insulin chains as discrete individual peptide moieties and insulin chains. More specifically, preferred chimeric fusion proteins of the invention, when tested in an assay in a mouse model of IDDM, provide a greater reduction in the frequency of onset of diabetes than a control mixture containing equimolar amounts of each of the various discrete individual peptide moieties and insulin chains comprised by the chimeric fusion protein, each of said individual peptide moieties and insulin chains not being covalently bound to any other of said individual peptide moieties and insulin chains in said mixture, wherein the assay is carried out by the repeated parenteral administration of a number of measured doses, each dose being of a predetermined molar quantity of said chimeric fusion protein in a pharmaceutically effective carrier or of said control mixture in the pharmaceutically effective carrier, the administration being at intervals of not less than twelve hours and not more than 72 hours between each of the doses.

As used herein, the phrase "the same peptides and insulin chains as discrete individual peptide moieties," used in comparison to a particular chimeric fusion protein of the invention, indicates a combination of isolated peptides and insulin chains that are not covalently linked together (e.g., by peptide bonds), wherein linking (via peptide bonds) the peptides and insulin chains together in the appropriate order {e.g., the same relative position in the amino terminal to carboxyl terminal sequence as found in full length GAD 65 and full length insulin chains) would produce the particular chimeric fusion protein of the invention.

While not wishing to be bound by any particular theory of operation, it is believed that complex in vivo antigen processing and presentation effects are responsible for the unexpected synergistic effects resulting from combining GAD 65 and insulin peptides and/or polypeptides into a single chimeric fusion protein.

The chimeric fusion proteins of the invention each combine in a single molecular entity the key (immunodominant) autoantigenic epitopes of both insulin and GAD 65. In so doing, they provide single component diagnostic and therapeutic compounds. The chimeric fusion proteins of the invention provide enhanced beneficial effects after administration to animals (including human patients) when compared to the administration of combinations of the individual peptides representing the same immunodominant epitopes as are comprised within the chimeric fusion proteins.

The preferred chimeric fusion proteins of the invention comprise insulin chain B (e.g., amino acids 1-31 of human insulin) and preferably further comprise insulin chain C (the "C fragment", e.g., amino acids 32-38 of human insulin). Amino acid sequences of insulin chains are known. See, for example, U.S. Pat. No. 4,431,740, which is incorporated herein by reference for the description of insulin chains and the content of the insulin sequences therein. See also U.S. Pat. No. 5,008,241, which is incorporated herein for its descriptions and sequences of insulin analogues, which analogues may be substituted for naturally occurring insulin chains in the chimeric fusion proteins of the present invention.

The chimeric fusion proteins of the invention further comprise at least one GAD peptide (i.e., polypeptide polymers of at least ten contiguous amino acids having a sequence identical to a contiguous sequence of at least ten amino acids found in GAD) that is covalently linked (preferably by peptide bonds) to the insulin chain, chains, analogues or peptides.

In accordance with the invention, the at least one GAD peptide is a GAD 65 peptide (i.e., a GAD peptide wherein the contiguous sequence of at least ten amino acids found in GAD is found in GAD 65). Preferably the GAD 65 peptide is a human GAD 65 peptide. Preferably the GAD 65 peptide is selected from the group consisting of human GAD 65 peptides 115-127 (a peptide corresponding to amino acid residues 39-50 of SEQ ID NO:2), 247-286 (a peptide corresponding to amino acid residues 51-90 of SEQ ID NO:2), and 473-519 (a peptide corresponding to amino acid residues 92-144 of SEQ ID NO:2). Complete amino acid sequences of GAD 65 polypeptides are known. See, for example, U.S. Pat. No. 5,691,448, which is incorporated herein by reference, particularly for the content of the sequence listings therein.

Results of studies described below suggest that the inclusion of human GAD 65 peptide 520-555 (a peptide with an amino acid sequence corresponding to amino acid residues 139-173 of SEQ ID NO:2) has a deleterious effect upon the immunomodulatory outcome of administration of insulin and GAD proteins or peptides. Accordingly, while within the scope of the invention, chimeric fusion proteins comprising human GAD 65 peptide 520-555 are disfavored. Preferably, the chimeric fusion proteins of the invention do not comprise a peptide sequence corresponding to GAD 65 peptide 520-555. It is also preferred that the chimeric fusion proteins of the invention do not include peptide sequences corresponding to those human GAD 65 peptides (particularly those amino terminal GAD 65 peptides) identified as inhibiting GAD solubility in U.S. Pat. No. 5,691,448 (which is incorporated herein by reference, particularly for its teachings in this regard) and do not contain peptide regions of GAD 65 that are associated with the pathogenesis of Stiff-Man syndrome. Thus, in accordance with the teachings of Butler et al., 1993, regarding dominant epitopes of GAD recognized by autoantibodies in Stiff-Man syndrome, the preferred chimeric fusion proteins of the invention do not include peptide regions comprising amino acids 1-95 of GAD 65; additionally, they do not include peptide regions comprising either or both of amino acids 475-484 or 571-585 of GAD 65.

Preferably the GAD peptides are arranged adjacently to each other (i.e., without more than about three intervening amino acids between them) in the same order as they are found in GAD 65, and the insulin chains are arranged adjacently to each other in the same order as they are found in preproinsulin. An arrangement where the insulin chains are amino terminal to the GAD peptides is also preferred in certain embodiments of the invention.

In certain preferred embodiments of the invention, at least one (preferably each) of the cysteine residues in the amino acid sequences of the various antigens and antigenic peptides combined to form the chimeric fusion proteins of the invention is replaced with an uncharged amino acid (i.e., an amino acid that is uncharged at a pH of between 6 and 7) having a molecular weight of less than about 150. In another preferred embodiment, none of such cysteine residues are replaced, i.e., there are no substitutions made for any cysteine residues present in any of the various antigens and antigenic peptides combined to form the chimeric fusion protein. When cysteine residues are replaced, the uncharged amino acid is preferably a standard amino acid. Preferably the standard amino acid is alanine or serine. Preferably the replacement of cysteine with another neutral amino acid is an epitope neutral replacement, i.e., it does not result in epitope conversion in any of the known immunodominant epitopes of the chimeric fusion protein, particularly those of GAD or insulin.

Detailed discussions of epitope neutral replacements and epitope conversion can be found in copending U.S. application Ser. No. 08/431,644, filed May 2, 1995 in the names of Steven H. Nye et al., for example at pages 34-36 of the specification of that application as filed. Also see copending U.S. patent application Ser. No. 08/482,114, filed Jun. 7, 1995 in the names of John P. Mueller et al. Those of skill in the art will readily comprehend the application of the teachings therein to the chimeric fusion proteins of the present invention. Accordingly, copending U.S. patent applications Ser. Nos. 08/431,644 and 08/482,114 are incorporated herein by reference to more fully describe the epitope neutral amino acid replacements encompassed within the chimeric fusion proteins of the present invention.

It is a further object to provide immunomodulatory methods for both the prevention and treatment of Type 1 diabetes mellitus and the amelioration of the autoimmune defects underlying this disease. Accordingly, it is an additional object of the invention to provide for the use of the chimeric fusion proteins of the invention in the manufacture of immunomodulatory medicaments.

To achieve these and other objects, the invention provides methods of treating a patient in need of such treatment, e.g., a patient selected from the group of patients consisting of patients at risk of developing type 1 diabetes and patients suffering from type 1 diabetes, so as to delay the onset or reduce the symptoms of diabetes in the patient and/or to ameliorate the autoimmune destruction of pancreatic beta cells in treated patients. Such treatment is particularly advantageous, and is preferably carried out, during the "honeymoon period" early in disease progression, before all of the patient's beta cells have been destroyed by the disease, or later in disease progression, when a patient is a candidate for transplantation of islet cells or tissues containing such cells.

These methods comprise the administration of at least one polypeptide of the invention to the patient. In one preferred embodiment, such administration is carried out on a therapeutic T cell modulatory schedule, i.e., a schedule designed to induce apoptosis, anergy, or other modulation of the autoimmune activity of T cells reactive with at least one epitope of the at least one polypeptide. Particulars of such therapeutic T cell modulatory schedules are discussed below. Other preferred methods of treatment of the invention include administration of at least one polypeptide of the invention to the patient via oral, intravenous, or, preferably, subcutaneous routes, or via parenteral administration with or preferably without an adjuvant such as Freund's incomplete adjuvant, Freund's complete adjuvant, alum adjuvant, or other immunogenic adjuvants now known or subsequently developed.

DETAILED DESCRIPTION OF THE PREFERRED EMBODIMENTS

Chimeric fusion proteins All polypeptides synthesized in biological systems are initially made with an N-terminal methionine residue. The extreme N-terminal and C-terminal amino acid residues are not considered essential to the functional use of the polypeptides of the invention, which, although not particularly preferred, may be produced without such residues. For example, the polypeptides may be chemically synthesized without N-terminal methionines. Preferred chimeric proteins of the invention thus include IG1 (comprising amino acid residues starting at about residue 2 and ending at about residue 153 of SEQ ID NO:1), IG2 (comprising amino acid residues starting at about residue 2 and ending at about residue 173 of SEQ ID NO:2), IG3 (comprising amino acid residues starting at about residue 2 and ending at about residue 137 of SEQ ID NO:3), IG4 (comprising amino acid residues starting at about residue 2 and ending at about residue 175 of SEQ ID NO:4), IG5 (comprising amino acid residues starting at about residue 2 and ending at about residue 226 of SEQ ID NO:5), IG6 (comprising amino acid residues starting at about residue 2 and ending at about residue 387 of SEQ ID NO:6) and IG7 (comprising amino acid residues starting at about residue 2 and ending at about residue 439 of SEQ ID NO:7). Preferably IG1 comprises amino acid residues 1-154 of SEQ ID NO:1, IG2 comprises amino acid residues 1-174 of SEQ ID NO:2, IG3 comprises amino acid residues 1-138 of SEQ ID NO:3, IG4 comprises amino acid residues 1-175 of SEQ ID NO:4, IG5 comprises amino acid residues 1-226 of SEQ ID NO:5, IG6 comprises amino acid residues 1-387 of SEQ ID NO:6, and IG7 comprises amino acid residues 1-438 of SEQ ID NO:7.

In certain preferred embodiments these chimeric proteins further comprise a histidine tag (i.e., a stretch of at least five and preferably six contiguous histidine residues, which facilitates the purification of the chimeric fusion protein by metal chelation chromatography). Preferably the histidine tag is located at the extreme C-terminus of the chimeric fusion protein. Histidine tags are discussed in greater detail in copending U.S. patent applications Ser. Nos. 08/431,644 and 08/482,114, which are incorporated herein by reference to more fully describe such histidine tag sequences and their uses.

Accordingly, in certain of these preferred embodiments IG1 comprises amino acid residues 1-160 of SEQ ID NO:1 and has a predicted molecular weight of about 18.8 kDa, IG2 comprises amino acid residues 1-180 of SEQ ID NO:2 and has a predicted molecular weight of about 21.2 kDa, IG3 comprises amino acid residues 1-144 of SEQ ID NO:3 and has a predicted molecular weight of about 17.1 kDa, IG4 comprises amino acid residues 1-181 of SEQ ID NO:4 and has a predicted molecular weight of about 19.8 kDa, IG5 comprises amino acid residues 1-232 of SEQ ID NO:5 and has a predicted molecular weight of about 25.3 kDa, IG6 comprises amino acid residues 1-393 of SEQ ID NO:6 and has a predicted molecular weight of about 43.7 kDa, and IG7 comprises amino acid residues 1-444 of SEQ ID NO:7 and has a predicted molecular weight of about 49.2 kDa.

Secondary Structure Considerations In designing IG4 (SEQ ID NO:4), IG5 (SEQ ID. NQ:5), and IG6 (SEQ ID NO:6), particular attention was paid to the predicted secondary structures of the polypeptides of the invention. IG4 was initially designed by hypothetically joining peptide epitopes of interest to form a single hypothetical sequence, IG4NHB (SEQ ID NO:8).

Secondary structure prediction of IG4NHB (SEQ ID NO:8) according to Chou and Fasman, 1978; Chou 1990; and Garnier et al., 1978; was performed using LASERGENE sequence analysis software (DNASTAR, Madison Wisc.). This algorithm predicts secondary structure of proteins from their amino acid sequences. Other sequence analysis software may also be used for this purpose, including other commercially available software such as GCG or MACVECTOR.

The entire sequence from amino acid 77 (Phe 77) to amino acid 134 (Thr 134) of IG4NHB (SEQ ID NO:8) was predicted to have helix forming characteristics. The propensity for actual long helix formation diminishes very rapidly for sequences higher than 20 amino acids, with the longest unbroken helices typically containing no more than 26 amino acids. The 57 amino acid helix-forming sequence from amino acid 77 to 134 of IG4NHB (SEQ ID NO:8) would thus be expected to break at unpredictable, if not random, points so as to form a variety of different structures. Such structures are undesirable in the chimeric fusion proteins of the invention, as they would be likely to be prone to uncontrollable aggregation and would be expected to differ from the native secondary structures of the epitopes in the isolated peptides comprised by the chimeric fusion proteins of the invention and in the native proteins from which the peptides are derived (e.g., insulin, GAD 65, or IA-2), which native secondary structures are preferred for the epitopes contained within the chimeric fusion proteins of the invention. Therefore, in certain preferred embodiments of the invention, helix breakers (see following paragraph) are inserted between the epitopes to 1) block the formation of a very long helix and 2) to predictably separate the epitopes into distinct structural entities with distinct secondary structures.

Helix breakers are amino acids, or groups of sequential amino acids that act to block the propagation of helical secondary structures in nascent polypeptide chains. Gly and Pro are known to be strong helix breakers, Asn and Tyr are weak helix breakers. The insertion of any of these amino acids or combinations thereof in a polypeptide will tend to cause a nascent polypeptide secondary structure helix to terminate at the point of the insertion. To assure helix termination and the separation of the desired epitopes, a helix breaker that is at least two amino acids long (wherein each of the amino acids is the same or different from the other and is selected from the group consisting of Gly, Pro, Asn, and Tyr) is preferred, more preferably, such a helix breaker is at least three amino acids long. Most preferably, the helix breaker is exactly three amino acids long. Highly preferred helix breakers are Pro-Pro-Pro (SEQ ID NO:9) and Gly-Gly-Gly (SEQ ID NO:10), with the latter being the most preferred of these.

Dosage In accordance with the present invention, when used as therapeutic agents, the chimeric proteins of the invention are administered to patients in need of such treatment in amounts ranging from about 6.9 pM/kg/patient to about 8.6 µM/kg/patient. Preferably the amounts range from about 34.5 pM/kg/patient to about 5.2 µM/kg/patient. More preferably the amounts range from about 170 pM/kg/patient to about 3.5 µM/kg/patient. Most preferably the amounts range from about 0.5 µM/kg/patient to about 3.5 SM/kg/patient.

In certain of its aspects, the present invention also provides for the repeated administration of doses containing lower amounts of the chimeric fusion proteins of the invention to a patient in need of such treatment. Although less preferred, doses containing amounts of below about 6.9 pM/kg/patient, and as low as about 1 pM/kg/patient may be used in the practice of the present invention.

Preferably the chimeric proteins are administered without the concomitant administration of an adjuvant, however, when used to perform T cell assays (e.g., in transgenic mice such as described in Wong et al. 1998), initial administration to experimental animals is preferably made with adjuvant.

Administration on Therapeutic T Cell Modulatory Schedules In accordance with the invention, a therapeutic T cell modulatory schedule involves administration of doses containing the chimeric proteins of the invention, preferably in a pharmaceutically effective carrier, repeatedly to the patient, at least two times at an interval of at least six, and preferably at least twelve hours, with an interval of not more than seven days, preferably not more than 72 hours, more preferably not more than 48 hours, and most preferably not more than 24 hours between doses.

In accordance with the present invention, the chimeric fusion proteins of the invention are preferably administered parenterally without the concomitant administration of an adjuvant. Administration by a parenteral route will typically be via injection such as intravascular injection (e.g., intravenous infusion), subcutaneous injection, or intramuscular injection. Other non-oral routes of administration, e.g., mucosal, inhalation, transdermal ultrasound, and the like, may be used if desired and practicable for the particular polypeptide to be administered.

Although less preferred, the chimeric fusion proteins of the invention may also be administered orally, however dosages for oral administration will typically be one to two orders of magnitude higher that those discussed above under the subheading "Dosage."

Formulations suitable for injection and other routes of administration are well known in the art and may be found, for example, in *Remington's Pharmaceutical Sciences*, Mack Publishing Company, Philadelphia, Pa., 17th ed. (1985). Preferred formulations for parenteral administration of the proteins of the invention are those described for insulin in the USP 23/NF 18 {1995).

Parenteral formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. Formulations may also contain pharmaceutically acceptable auxiliary substances as required, such as, tonicity adjusting agents, wetting agents, bactericidal agents, preservatives, stabilizers, and the like.

Further discussions of dosage and administration of polypeptides using therapeutic T cell modulatory schedules may be found in copending U.S. patent applications Ser. Nos. 08/431,644 and 08/482,114 (discussed above) and copending U.S. patent application Ser. No. 08/565,769, filed Dec. 1, 1995 in the name of Yi Wang, each of which is hereby incorporated herein by reference in its entirety to more fully describe the state of the art to which the present invention pertains.

Without intending to limit it in any manner, the present invention will be more fully described by the following examples.

Experimental Methods Non-obese diabetic (NOD) mice are a strain of mice that are prone to the development of diabetes, and represent an accepted model system for the study of diabetes mellitus. These mice, designated NOD/MrkTacfBR, were purchased from Taconic Farms (Germantown, N.Y.). NOD SCID mice, designated NOD/SCID, are available from the Jackson Laboratories, Bar Harbor, Me. The incidence of diabetes by 200 days of age in these mice is 80% in females and 50% in males. At 110 days of age, fewer than 15% of the male NOD mice became diabetic.

CYTOXAN induction experiments: CYTOXAN (Cyclophosphamide) treatment can increase the incidence and accelerate the onset of diabetes in non-diabetic NOD mice. Randomly selected, non-diabetic male NOD mice, which were 100 to 110 days of age, were injected (ip) with cyclophosphamide (250 mg/kg) on day 0.

All the mice were subjected to urine glucose measurement 2-3 times per week for a period of 21 days after cyclophosphamide injection. The onset of diabetes was recorded as the first point at which two consecutive days of positive urine glucose results were obtained. Blood glucose was also measured to confirm the urine glucose results. (ExacTech, MediSense Inc., Cambridge, Mass.) In all the mice tested with positive urine glucose, blood glucose levels were greater than 15 omg/dl. At day 21, these mice were sacrificed and examined histologically.

Experiments in the NOD/SCID Adoptive Transfer Model: Spleen mononuclear cells were harvested from diabetic NOD mice of recent disease onset (diabetic not more than 3 weeks) and about $35 \times 10^6$ of these spleen cells in 0.2 ml of PBS were injected intravenously into 6-8 week old NOD/SCID mice. Onset of diabetes was monitored biweekly by urine glucose testing and confirmed by blood glucose testing on day 28 relative to the time of spleen cell transfer. At day 28, these mice were sacrificed and examined histologically.

Reagents: CYTOXAN (cyclophosphamide, Mead Johnson oncology products) was dissolved in distilled water (25 mg/ml). Oxidized bovine insulin Chain B was purchased from Sigma (catalog no. I-6383). Both insulin chain B and the BSA control protein (Miles Inc., #81-001) were dissolved in PBS/1M HCL, pH2, before dialysis against PBS, pH7.2, sterile filtration, and storage of frozen aliquots.

EXAMPLES

Genes for Expression of Chimeric Proteins of the Invention

IG1. A synthetic chimeric gene encoding chimeric protein IG1(SEQ ID NO:1) was constructed in two rounds of overlapping PCR (Ho et al., 1989). Each gene subdomain was synthesized in a standard PCR 100 μl reaction using 10 pmole of each of the appropriate oligonucleotide primers, as described below. The 5' gene segment was amplified using the overlapping primers:prIG1 (SEQ ID NO:11), and prIG2 (SEQ ID NO:12). The 3' gene segment was amplified using the overlapping primers prIG3 (SEQ ID NO:13) and prIG4 (SEQ ID NO:14). The prIG1 oligo-nucleotide (SEQ ID NO:11) was designed to allow creation of a unique NdeI restriction site at the 5' end. The prIG4 primer (SEQ ID NO:14)included a unique BamHI site, stop codon (TAA) and 18 nucleotides that encoded a histidine tag sequence for purification of the recombinant chimeric protein by metal affinity chromatography. The two subdomains were combined using flanking oligonucleotides prIG5 (SEQ ID NO:15) and prIG6 (SEQ ID NO:16) in a second PCR reaction to yield a 492 bp gene product. The PCR product was cloned into expression plasmid vector pCR2.1 as described by the supplier (Invitrogen, San Diego, Calif.). Kanamycin-resistant DH10B transformants were selected and the correct clones and orientations determined by restriction and sequence analysis. Restriction fragments from two clones (#6 and #18) were combined to remove undesired mutations. Following nucleotide sequence analysis, an independent plasmid pCR2.1-IG1 was digested with NdeI and BamHI and the 492 bp fragment inserted into compatible sites of the MP4 expression plasmid pET22b-MP4 (Elliott et al., 1996), yielding plasmid pIG1. The insert from pCR2.1-IG1 was also subcloned into plasmid vector pBLUSCRIPT®SK+ (STRATAGENE CLONING SYSTEMS, La Jolla, Calif.) to yield plasmid pSK+IG1. The synthetic IG1 gene (SEQ ID NO:17) encodes a chimeric fusion protein with a predicted mass of about 18.8 kDa.

IG2. A synthetic chimeric gene encoding chimeric protein IG2 (SEQ ID NO:2) was constructed by PCR amplification of an internal IG1 gene fragment using pIG1 as a template along with the sense primer prIG7 (5'-AGATCTGATG AACAT-TCTGC TGCAGTATGT TGTTAAAAGC TTCGATAACA TGTATGCCAT GATG-3'-SEQ ID NO:18; BglII site underlined) in combination with the anti-sense oligonucleotide primer prIG8 (5'-TGTACAGATA TCCGCCAGT TCCAGA-CATT TTTTCAGAGA AAAATGGCTA TGTTCAGAGG TAAAGGCAAT CAGACGCG-3'-SEQ ID NO:19; BsrGI site underlined). The 197 bp BglII-BsrGI PCR fragment was subcloned into pCR2.1. Sequence analysis revealed a C>G substitution at position 183 in the coding strand of the 197 bp BglII-BsrGI PCR fragment for all subclones analyzed, and the plasmid was named pCR2.1-IG7/8C183G. Subsequent analysis revealed an error in the original prIG8 primer sequence (SEQ ID NO:19). A repair primer, prIG12 (SEQ ID NO:20), was synthesized to correct the C>G substitution in pCR2.1-IG7/8C183G. The internal 197 bp BglII-BsrGI DNA segment was corrected by PCR using pCR2.1-IG7/8C183G as a template along with primers prIG7 (SEQ ID NO:18) and prIGl2 (SEQ ID NO:20). The PCR fragments were subcloned into pCR2.1, their sequence was determined using standard dideoxy sequencing to confirm that the desired sequence had been obtained, and a single clone designated pCR2.1-IG7/12 was isolated and amplified.

The 137 bp BglII-BsrGI restriction fragment in pSK+IG1 was exchanged with the 197 bp BglII-BsrGI fragment from pCR2.1-IG7/12 to create pSK+/IG7/12. The 552 bp NdeI-BamHI fragment from pSK+/IG7/12 was subcloned into the compatible sites of pIG1 to create plasmid pIG2. The synthetic IG2 gene (SEQ ID NO:21) encodes a chimeric fusion protein with a predicted mass of about 21.2 kDa.

IG3. A synthetic chimeric gene encoding chimeric protein IG3 (SEQ ID NO:3) was constructed by removing a 552 bp NdeI-BamHI restriction fragment from plasmid pET22b-IG2 and substituting an NdeI-BamHI digested 444 base pair PCR product therefor. This 444 base pair PCR product was made using primers prIG5 (SEQ ID NO:15) and prIG13 (SEQ ID NO:22) with the synthetic IG2 gene as a template. The synthetic IG3 gene (SEQ ID NO:23) encodes a chimeric fusion protein with a predicted mass of about 17.1 kDa.

IG4. A gene sequence encoding chimeric protein IG4 (SEQ ID NO:4) is set forth below as SEQ ID NO:24, and encodes a chimeric fusion protein with a predicted mass of about 19.8 kDa.

IG5. A synthetic chimeric gene encoding chimeric protein IG5 (SEQ ID NO:5) was constructed via ligation of PCR products using primers prIG14 (SEQ ID NO:25), prIG15 (SEQ ID NO:26), prIG16 (SEQ ID NO:27), prIG17 (SEQ ID NO:28), prIG18 (SEQ ID NO:29), prIG19 (SEQ ID NO:30), prIG20 (SEQ ID NO:31), prIG21 (SEQ ID NO:32), prIG22 (SEQ ID NO:33), and prIG23 (SEQ ID NO:34). The synthetic IG5 gene (SEQ ID NO:35) encodes a chimeric fusion protein with a predicted mass of about 25.3 kDa.

IG6. A gene sequence encoding chimeric protein IG6 (SEQ ID NO:6) is set forth below as SEQ ID NO:36, and encodes a chimeric fusion protein with a predicted mass of about 43.7 kDa.

IG7. A gene sequence encoding chimeric protein IG7 (SEQ ID NO:7) is set forth below as SEQ ID NO:37, and encodes a chimeric fusion protein with a predicted mass of about 49.2 kDa.

Expression and purification of recombinant IG fusion proteins. For each IG fusion protein expression plasmid construction that was bacterially expressed, electrocompetent *E. coli* strain BL21(DE3) was transformed with the expression plasmid and ampicillin-resistant colonies were selected for liquid culture. The 1DE3 lysogen in strain BL21(DE3) contains the gene for T7 polymerase behind the *E. coil* lacUV5 promoter for efficient expression of target genes under control of the strong bacteriophage T7 transcriptional and translation signals (Studier et al., 1990).

The recombinant chimeric fusion protein was purified from solubilized whole cell pellets by immobilized metal affinity chromatography and analyzed by SDS-PAGE/Coomassie blue staining. Four liters cultures were grown to OD600 of 0.8 in Terrific Broth (TB) medium (Sambrook et al., 1992). Protein expression was induced for 5 hours with 1 mM isopropylthiogalactoside (IPTG). Induced cells were harvested by centrifugation and frozen overnight at −20° C. Cell pellets were thawed at room temperature and homogenized in 10 ml/g of Buffer A (6 M guanidine-HCl/10% glycerol/20 mM Tris-Cl pH 7.8/500 mM NaCl/200 mg sodium sulfite/280 mg sodium tetrathionate) using a TEK-MAR homogenizer (The Tekmar Co., Cincinnati, Ohio). Cells were frozen at −70° C. for 1 hour and thawed at room temperature to promote cell lysis. The cell suspension was gently mixed for 30 min at room temperature using a magnetic stirrer. The soluble fraction containing IG protein was collected as the supernatant following centrifugation of the cell lysate at 10,000×g for 30 min at 4° C. in a Beckman JA-10 rotor. The supernatant was loaded on a Ni—NTA (QIAGEN Inc., Chadsworth, Calif.) column previously equilibrated in Buffer A at a flow rate of 8 ml/min. The column was washed to baseline absorbance using Buffer A. The column was further washed with Buffer B (6 M urea/10% glycerol/20 mM Tris-Cl/500 mM NaCl pH 7.8) and contaminating *E. coli* proteins were removed with Buffer C (6 M urea/10% glycerol/20 mM Tris-Cl/500 mM NaCl pH 5.0). IG protein was eluted with Buffer D (6 M urea/10% glycerol/20 mM Tris-Cl/500 mM NaCl pH 4.0). All fractions were collected in batch and analyzed on a 4-20% SDS-polyacrlyamide gradient gel in the presence of reductant. The IG containing fractions (Buffer D wash) were concentrated 10-fold using an AMICON STIRCELL using a PM10 membrane. The sample was dialyzed against two changes of MILLI-Q water at 4° C. The IG preparations were filter sterilized and the concentration determined spectrophotometrically using a conversion factor of 1.06 mg/ml/$OD_{280}$. Five micrograms were analyzed under reducing and nonreducing conditions by SDS-PAGE so as to obtain an initial indication of purify and integrity of the protein preparations.

Figure 2:
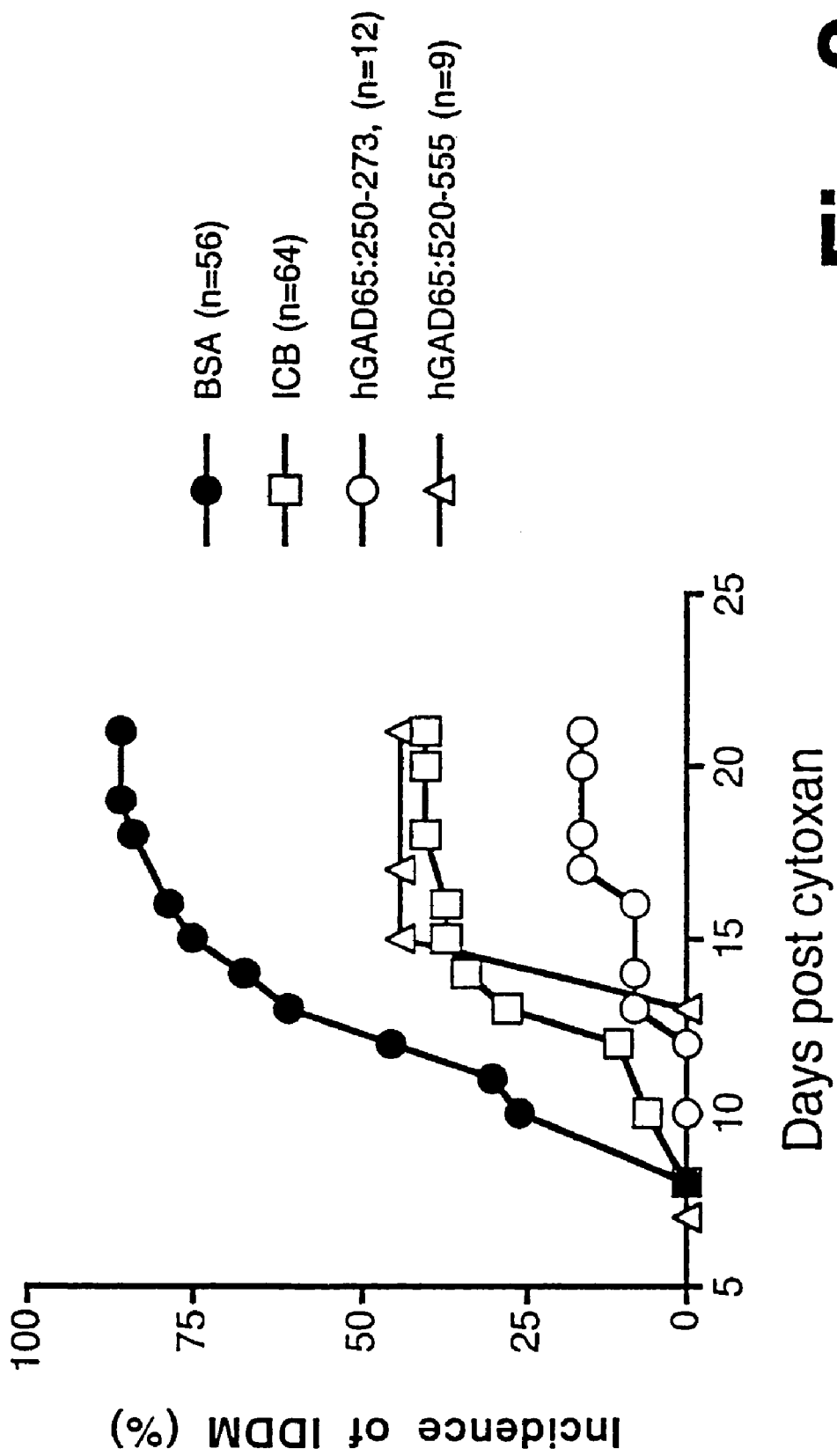
FIG. 2 shows the results of CYTOXAN (cyclophosphamide) induced IDDM experiments in which NOD mice were treated with bovine serum albumin (BSA, as control) insulin chain B (ICB) human GAD 65 peptide 250-273, or human GAD 65 peptide 520-555 (a peptide with a sequence corresponding to amino acid residues 139-173 of SEQ ID NO:2).
Figure 3:
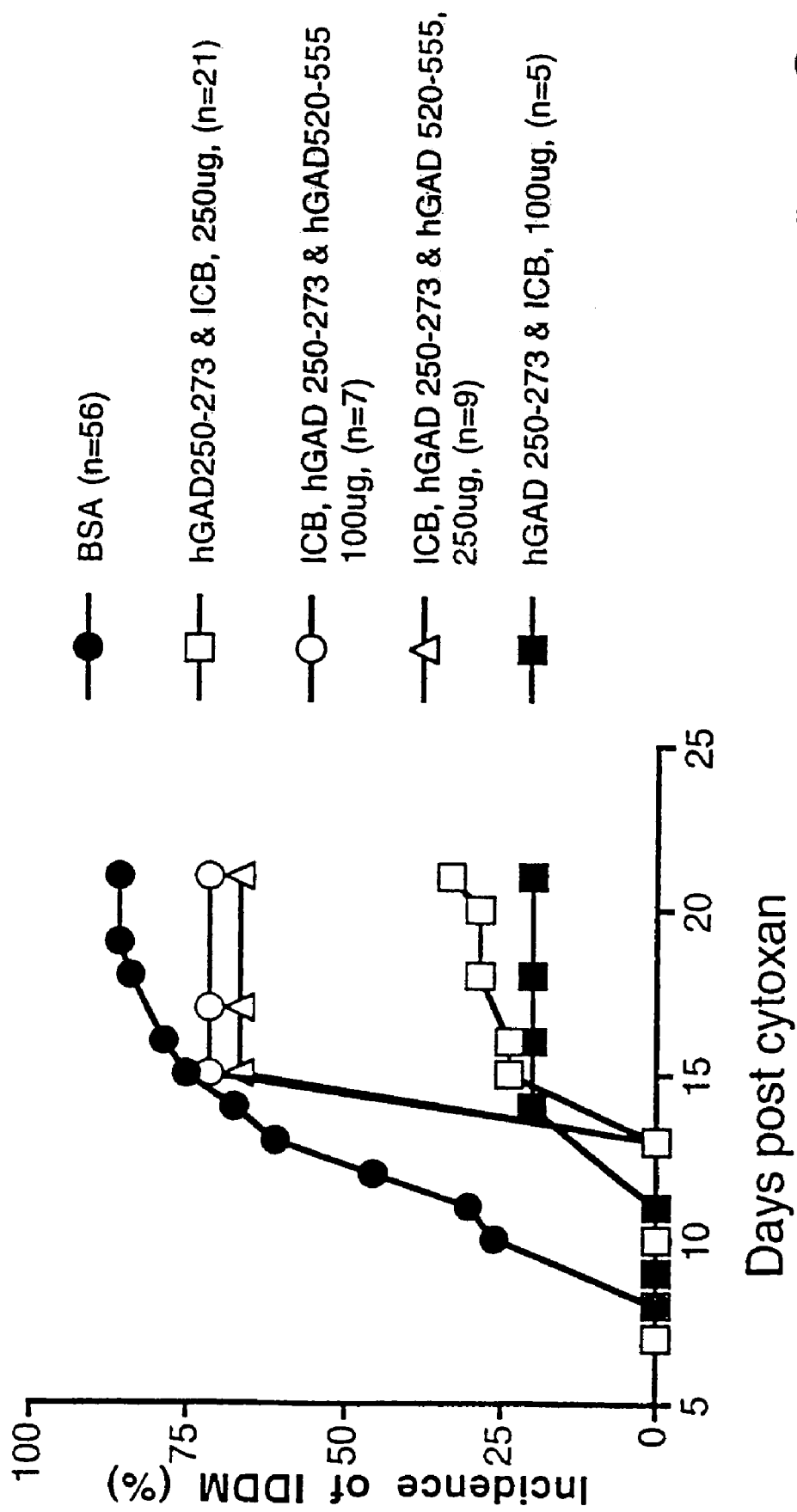
FIG. 3 shows the results of CYTOXAN (cyclophosphamide) induced IDDM experiments in which NOD mice were treated with bovine serum albumin (BSA, as control) or the following mixtures of insulin chain B (ICB) and human GAD 65 peptides: 1)100 μg each of ICB and human GAD 65 peptide 250-273, 2) 250 μg each of ICB and human GAD 65 peptide 250-273, 3)100 μg each of ICB, human GAD 65 peptide 250-273, and human GAD 65 peptide 520-555, and 4) 250 μg each of ICB, human GAD 65 peptide 250-273, and human GAD 65 peptide 520-555.

Chimeric fusion protein treatment—CYTOXAN (cyclophosphamide) model: Groups of randomly selected NOD mice were injected intravenously twice daily with either BSA as a control, or GAD peptides, insulin chain B (ICB) or various combinations of GAD peptides and/or insulin chain B at the doses indicated in the figures on days 1, 3, and 5 following CYTOXAN (cyclophosphamide) treatment (day 0). Animals that received injections of BSA (controls) manifested a greater than 80% incidence of diabetes by 21 days following CYTOXAN (cyclophosphamide) induction (FIG. 2). In contrast, animals treated with either ICB or either of GAD 65 250-273 or 520-555 peptides, experienced reductions to less than 50% incidence of diabetes. The therapeutic effects of treatment with combinations of ICB and the two GAD peptides were then examined (FIG. 3). Reduction in diabetes incidence to 25% or less was achieved by the combination of GAD 250-273 and ICB at doses of 100 μg or 250 μg per injection.

Figure 4:
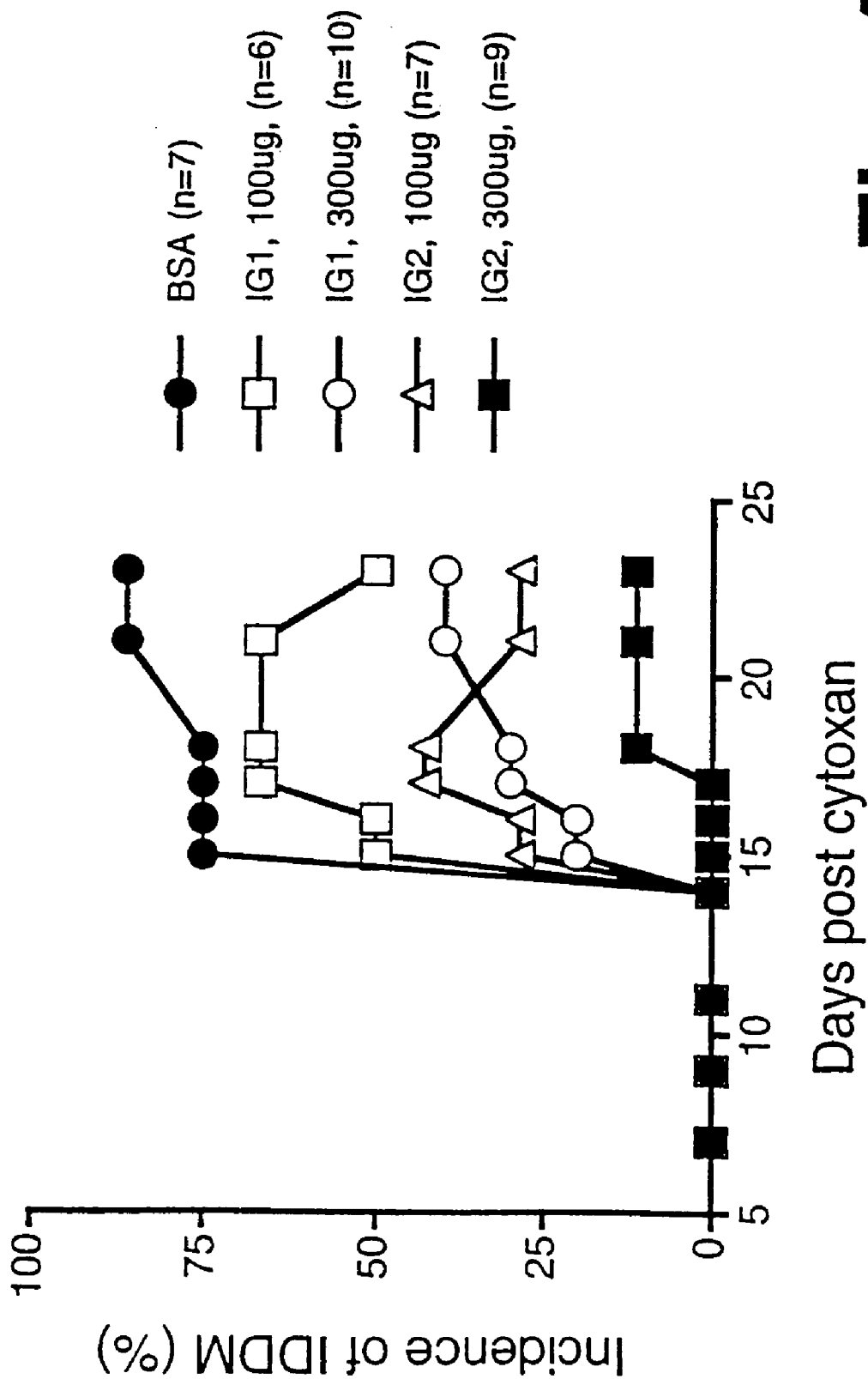
FIG. 4 shows the results of CYTOXAN (cyclophosphamide) induced IDDM experiments in which NOD mice were treated with bovine serum albumin (BSA, as control) or 100 μg of the IG1 chimeric protein, 250 μg of the IG1 chimeric protein, 100 μg of the IG2 chimeric protein, or 250 μg of the IG2 chimeric protein.

Surprisingly, the addition of GAD peptide 520-555 (amino acid residues 139-173 of SEQ ID NO:2) appeared to inhibit the therapeutic efficacy of the ICB with GAD 65 250-273 combination. Evaluation in the CYTOXAN (cyclophosphamide) model of the IG1 and IG2 chimeric fusion proteins of the invention, showed that treatment with either of these polypeptides mediated a dose-dependent reduction in the incidence of diabetes compared to the BSA treated control animals FIG. 4. In this experiment, 300 ug doses were more effective than 100 ug doses, and IG2 reduced the incidence of diabetes to a greater degree than IG 1. Treatment with 300 ug doses of IG2 reduced disease incidence to less than 12%, compared to greater than 80% disease incidence in the BSA treated control animals.

Chimeric Fusion Protein Treatment—Adoptive Transfer Model:

Diabetogenic splenic mononuclear cells were harvested from newly diabetic NOD mice (onset less than 3 weeks previous). To initiate the destruction of islet beta cells and the development of diabetes, 8-12 week old NOD/SCID mice were injected intravenously with 35×10$^6$ diabetogenic spleen cells. The incidence and onset of diabetes were monitored biweekly by urine glucose testing and confirmed by blood glucose testing at the end of the experiment. The average onset time of diabetes after disease induction was approximately 25 days. IV treatment with IG2, IG3, or islet beta cell antigens was initiated on day 3. Animals were treated with 300 ugs of antigen twice daily every other day for a period of six days (from day 3 to day 9, where the time of spleen cell transfer was day 0).

Figure 5:
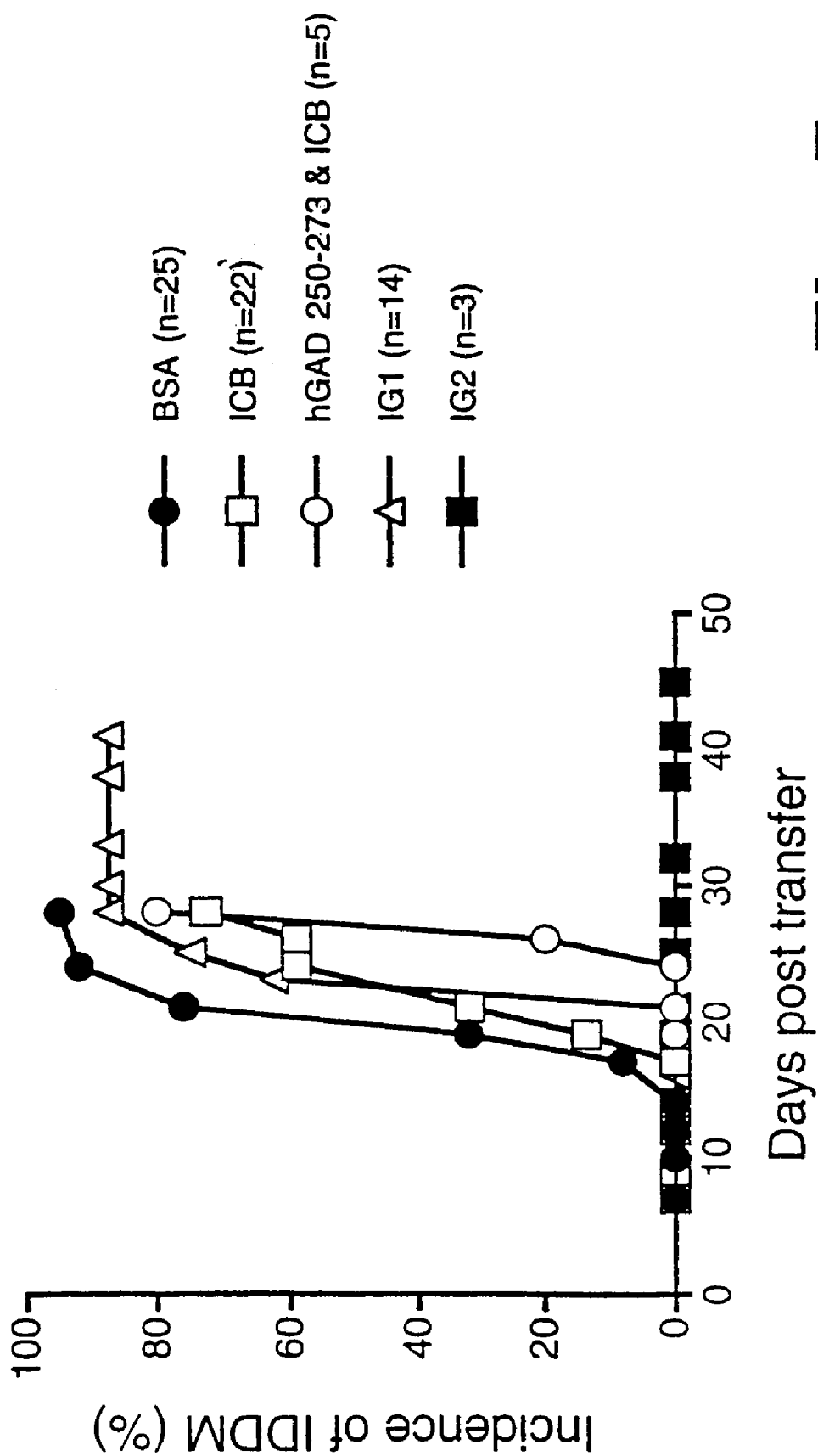
FIG. 5 shows the results of the adoptive transfer of IDDM experiments.
Figure 6:
FIG. 6 shows a schematic diagram of the IG4 fusion protein (SEQ ID. NO:4). The numbers following the backslashes in the legend indicate the position of the indicated peptide moiety component in native human GAD 65 from which its sequence was derived, while the aa numbers in parentheses the corresponding amino acid numbers in SEQ ID NO:4, and the notation GGG indicates the incorporation at that point of a three glycine helix-breaking linker.
Figure 7:
FIG. 7 shows a schematic diagram of the IG5 fusion protein (SEQ ID NO:5). The numbers following the backslashes in the legend indicate the position of the indicated peptide moiety component in native human GAD 65 from which its sequence was derived, while the aa numbers in parentheses the corresponding amino acid numbers in SEQ ID NO:5, and the notation GGG indicates the incorporation at that point of a three glycine helix-breaking linker.
Figure 8:
FIG. 8 shows a schematic diagram of the IG6 fusion protein (SEQ ID NO:6). The numbers following the backslashes in the legend indicate the position of the peptide component of the native human protein from which its sequence was derived, while the aa numbers in parentheses the corresponding amino acid numbers in SEQ ID NO:6, and the notation GGG indicates the incorporation at that point of a three glycine helix-breaking linker. As indicated in the legend, IG6 comprises, in addition to the indicated portions of human insulin and human GAD 65 (hGAD 65), a C-terminal portion of human IA-2 (hIA2) spanning amino acids 771-979 of the native human protein (amino acids 176-387 of SEQ ID NO:6), with a three glycine helix-breaking linker incorporated at the N-terminus of this portion of IA-2.
Figure 9:
FIG. 9 shows a schematic diagram of the IG7 fusion protein (SEQ ID NO:7). The numbers following the backslashes in the legend indicate the position of the peptide component of the native human protein from which its sequence was derived, while the aa numbers in parentheses the corresponding amino acid numbers in SEQ ID. NO:7, and the notation GGG indicates the incorporation at that point of a three glycine helix-breaking linker. As indicated in the legend, IG7 comprises, in addition to the indicated portions of human insulin and human GAD 65 (hGAD 65), a C-terminal portion of human IA-2 (hIA2) spanning amino acids 771-979 of the native human protein (amino acids 228-439 of SEQ ID NO:7), with a three glycine helix-breaking linker incorporated at the N-terminus of this portion of IA-2.

The results of these experiments are set forth in FIG. 5. They surprisingly demonstrate that only the IG2 chimeric fusion protein prevented the onset of disease in the NOD/SCID recipients. In contrast, in this model only a slight delay in disease onset was observed in recipients of IG1, insulin chain B (ICB), or the combination of ICB and GAD peptide 250-273. These profound differences in the effects of treatment with IG2 as compared to the other treatment regimens was unexpected. Without wishing to be bound by any particular theory of operation, it is believed that this unexpected finding is a result of the in vivo processing of IG2 into unique antigenic peptides that are particularly effective at eliciting a state of immune tolerance protective against autoimmune diabetes, even in the demanding conditions resulting from challenge with heterogeneous T cell populations derived from the spleens of fully diabetic NOD mice. Although preferred and other embodiments of the invention have been described herein, further embodiments may be perceived by those skilled in the art without departing from the scope of the invention as defined by the following claims.

REFERENCES

Abbas et al. 1991. *Cellular and Molecular Immunology* W. B. Saunders Company, Philadelphia.
Ammerer, 1983. *Meth Enzymol* 101:192 et seq.
Atkinson and MacLaren, 1993. *J Clin Invest* 92:1608-1616.
Atkinson et al., 1990. *Lancet* 335:1357-1360.
Atkinson et al., 1990. *Diabetes*, 39:933-937.
Atkinson et al., 1992. *Lancet* 339:458-459.
Atkinson et al., 1993. *J Clin Invest* 91:350-356.
Ausubel et al., 1994. *Current Protocols in Molecular Bioloqy*, John Wiley & Sons, New York.
Baekkeskov et al., 1982. *Nature* 298:167-169.
Baekkeskov et al., 1987. *J Clin Invest* 79:926-934.
Baekkeskov et al., 1990. *Nature* 347:151-156.
Bock et al., 1992. *Lancet* 339:1504-1506.
Boehme and Lenardo, 1993. *Eur J Immunol* 23:1552-1560.
Bonifacio et al., 1990. *Lancet*, 335:147-149.
Bowman et al., 1994. *Immunol Today* 15(3):115-120.
Brunner et al., 1995. Nature 373:441-444.
Butler et al., 1993. *J Exp Med* 178:2097-2106.
Chang et al., 1978. *Nature* 275:615 et seq.
Chen et al., 1994. *Science* 265:1237-1240.
Chou, 1990. *Prediction of Protein Structure and the Principles of Protein Conformation*, Plenum Press 549-586.
Chou and Fasman, 1978. *Adv. Enzymol.* 47:45-147.
Cohen et al., 1992. *Ann Rev Immunol* 10:267 et seq.
Coligan et al., 1995. *Current Protocols in Immunology* John Wiley 25 & Sons, New York.
Conrad et al., 1994. *Nature* 371:351-355.
Cotter et al., 1990. *Anticancer Research* 10:1153 et seq.
Crispe, 1994. *Immunity* 1:347-349.
Daniel et al., 1996. *Proc. Natl. Acad. Sci. USA* 93:956-960.
Davis et al., *Basic Methods in Molecular Biology*, 2nd ed. Appleton and Lange, Norwalk, Conn.
De Aizpurua et al., 1992. *Proc Natl Acad Sci, USA* 89:9841-9845.
Dhein et al., 1995. *Nature* 373:438-441.
Duvall and Wyllie, 1986. *Immunol Today* 7:115 et seq.
Elliott et al., 1996. *J Clin Invest* 98:1-11.

Evans and Scarpulla, 1989. *Gene* 84:135 et seq.
Farrell, Jr., 1993. *RNA Methodologies: A Laboratory Guide For Isolation And Characterization*. Academic Press Inc., San Diego, Calif.
Foster, 1994. in *Harrison's Principles of Int Med*, Thirteenth Ed., McGraw-Hill, New York, pp. 1979-2000.
Garnier et al., 1978. *J. Mol. Biol* 120:97-120.
Goeddel et al., 1980. *Nucl Acids Res* 8:4057 et seq.
Griffin and Griffin, Eds., 1994. *PCR Technology, Current Innovations*. CRC Press, Boca Raton, Fla.
Griffin et al., 1995. *Am. J. Pathol* 147:845-857.
Grosjean and Fiers, 1982. *Gene* 18:199 et seq.
Hanninen et al., 1992. *J Clin Invest* 90:1901-1910.
Harrison, 1992. *Immunol Today* 13:348-352.
Harwood, Ed., 1994. *Protocols For Gene Analysis: Methods In Molecular Biology, Vol.* 31. The Humana Press, Totowa, N.J.
Hatfield et al., 1997. *Diabetologia* 40:1327-1333.
Hernan et al. 1992. *Biochemistry* 31:8619 et seq.
Herold et al., 1992. *J Exp Med* 176:1107-1114.
Ho et al., 1989. *Gene* 77:51-59.
Honeyman et al., 1993. *J Exp Med* 177:535-540.
Huang and Gorman, 1990. *Mol Cell Biol* 10:1805 et seq.
Ju et. al., 1995. *Nature* 373:444-448.
Karjalainen et al., 1992. *New Eng J Med* 327:302-307.
Karounos and Thomas, 1990. *Nature* 39:1085-1090.
Kaufman et al., 1992. *J Clin Invest* 89:283-292.
Kaufman et al., 1993. *Nature* 366:69-72.
Kaufman et al., 1993. *Nature.* 366:69-71.
Kawabe and Ochi, 1991. *Nature* 349:245-248.
Kawasaki et al., 1997. *J. Clin. Endocrinol. Metab.* 82:375-380.
Kerr et al., 1991. *Apoptosis: The Molecular Basis Of Cell Death*, Tomei and Cope (eds.), Cold Spring Harbor Laboratory Press, Plainview, N.Y., pp. 5 et seq.
Kim et al., 1993. *Immunol Invest* 22(3):219-227.
Klaus, ed., 1987. *Lymphocytes: A Practical Approach. IRL Press, Oxford, England.*
Lenardo, 1991. *Nature* 353:858-860.
Lockshin and Zakeri, 1991. *Apoptosis: The Molecular Basis Of Cell Death*, Tomei and Cope (eds.), Cold Spring Harbor Laboratory Press, Plainview, N.Y., pp. 47 et seq.
Lohman et al., 1994. *Lancet.* 343:1607-1608.
Lohman et al., 1996. *J of Autoimmunity.* 9:385-389.
Lohmann et al., 1996. *Hormone & Metabolic Res.* 28:357-360.
Luckow et al., 1988. *Bio/Technology* 6:47 et seq.
MacLaren et al., PCT patent appl. Int. Pub. No. WO 94/23737.
MacLaren, N and K. Lafferty. 1993. *Diabetes.* 42:1099-1104.
Maniatis, 1982. *Molecular Cloning: A Laboratory Manual*. Cold Spring Harbor Laboratory, Cold Spring Harbor, N.Y.
Marrack and Kappler, 1987. *Science* 238:1073 et seq.
Moir et al., 1991. *Meth Enzymol* 194:491-507.
Morgenstern and Land, 1990. *Nucl Acids Res* 18:3587 et seq.
Mueller et al., U.S. application Ser. No. 08/482,114, filed Jun. 7, 1995.
Muir et al., 1995. *J Clin Invest* 95, pp.628-634.
Mullis et al., Eds., 1994. *The Polymerase Chain Reaction*. Springer-Verlag, New York, N.Y.
Nagata and Suda, 1995. *Immunol Today* 16:39 et seq.
Naquet et al., 1988. *J. Immunol.* 140:2569-2578.
Nossal et al., 1992. *Diabetologia, pp.* 549-559.
Ormerod, Ed., 1994. *Flow Cytometry: A Practical Approach,* 2nd ed. IRL Press at Oxford University Press, Oxford, England.

Paul, 1989. *Fundamental Immunology, 2nd Ed*. Paul (ed.), Raven Press, New York.
Quinn, A and E. E. Sercarz. 1996. *J. Autoimmunity* 9:365-370.
Ramiya et al., 1996. *J. Autoimmunity* 9:349-356.
*Remington's Pharmaceutical Sciences*, Mack Publishing Co., Philadelphia, Pa., 17th ed. (1985)
Richter et al., 1992. *Proc Natl Acad Sci*, USA 89:8467-8471.
Rudy et al., 1995. *Mol. Medicine* 1:625-633.
Russell et al., 1993. *Proc Natl Acad Sci USA* 90:4409-4413.
Sambrook et al., 1990. *Molecular Cloning: A Laboratory Manual* Cold Spring Harbor Press, Cold Spring Harbor, N.Y.
Sato et al., 1994. *J Biol Chem* 269:17267 et seq.
Schena, et al., 1991. *Meth Enzymol* 194:389-398.
Schwartz, 1993. Schwartz, R S, "Autoimmunity and Autoimmune Diseases" in Paul, *Fundamental Immunology*, 3rd Ed. Press, New York, 1993, pp. 1033-1097.
Sercarz et al., 1959. *Nature* 184:1080-1082.
Singer et al., 1994. *Immunity* 1:365-371.
Smith et al., 1989. *Nature* 337:181-184.
Solimena and De Camilli, 1993. *Nature* 366:15-17.
Steinman, 1995. *Cell* 80:7-10.
Strasser, 1995. *Nature.* 373:385-386.
Studier et al., 1990. *Meth Enzymol* 185:60-89.
Sun et al., 1991. *Eur J Immunol* 21:1461-1468.
Taguchi et al., 1990. *J Immunol Meth* 128:65-73.
Talib et al., 1991. *Gene* 98:289-293.
Tisch et al., 1993. *Nature.* 366:72-75.
Tisch et al., 1993. *Nature.* 366:72-75.
USP 23/NF 18, 1995. The United States Pharmacopeia/The National Formulary; United States Pharmacopeial Convention, Inc., Rockville, Md.
von Boehmer, 1988. *Ann Rev Immunol* 6:309 et seq.
Walston et al., 1995. *N Eng J Med* 333:343-347.
Walter et al., 1994. *J. Clin. Invest.* 8:163-166.
Weiner et al., 1997. U.S. Pat. No. 5,643,868.
Weir, 1978. *Handbook of Experimental Immunology*, 3rd ed. Volume 2, Cellular Immunology, Blackwell Scientific Publications, Oxford, England.
Wicker et al., 1996. *J. Clin. Invest.* 98:2597-2603.
Williams et al., 1988. *Nucl Acids Res* 16:10453 et seq.
Wong et al., 1998. *J. Clin Invest* 102:947-957.
Xie et al., 1997. *J. Immunol.* 159:3662-3667.
Zhang et al., 1997. *Diabetes* 46:40-43.
Zhang et al., 1991. *Proc Natl Acad Sci, USA* 88:10252-10256.

TABLE 1 dose dependency of cyclophosphamide induced diabetes in non-diabetic male NOD recipients

| CYTOXAN | # Diabetic/Total | % | Mean onset time |
|---|---|---|---|
| 200 mg/kg | 2/7 | 28.6% | 12 |
| 250 mg/kg | 5/7 | 71.4% | 11 |
| 300 mg/kg | 5/7 | 71.4% | 12.6 |

What is claimed is:

1. A method of treating a patient selected from the group consisting of patients predicted to be at risk of developing Type 1 diabetes and patients suffering from Type I diabetes, said method comprising the repeated administration of a dose of a measured amount of a chimeric fusion protein in a pharmaceutically effective carrier to said patient, said chimeric fusion protein comprising an amino terminus and a carboxyl terminus, wherein the protein comprises insulin chain B, the first 7 amino acid residues of insulin chain C, and individual peptide moieties consisting of at least two glutamate decarboxylase (GAD) 65 peptides capable of eliciting a human T cell response, wherein the insulin chain B, insulin chain C, and the at least two human GAD 65 peptides are covalently linked and the chimeric fusion protein is capable of eliciting a human T cell response to insulin chain B and to each of the at least two GAD 65 peptides.

2. The method of claim 1, wherein the GAD 65 peptide is selected from the group consisting of human GAD 65 peptides 115-127,247-286, and 473-519.

3. The method of claim 2, wherein the protein comprises, in order, starting at the amino terminus, human GAD 65 peptides 115-127, 247-286, and 473-519.

4. The method of claim 3, wherein the protein comprises, in order, starting at the amino terminus, insulin chain B, the first 7 amino acid residues of insulin chain C and human GAD 65 peptides 115-127, 247-286, and 473-519.

5. The method of claim 1, wherein the protein does not contain an amino acid sequence comprising the sequence of amino acid residues 139-173 of SEQ ID NO:2.

6. The method of claim 1, wherein, when tested in an assay in a mouse model of insulin dependent diabetes mellitus (IDDM), the chimeric fusion protein provides a greater reduction in the frequency of onset of diabetes than a control mixture containing equimolar amounts of each of the various discrete individual peptide moieties and insulin chains comprised by the chimeric fusion protein, each of said individual peptide moieties and insulin chains not being covalently bound to any other of said individual peptide moieties and insulin chains in said mixture, wherein the assay is carried out by the repeated parenteral administration of a number of measured doses, each dose being of a predetermined molar quantity of said chimeric fusion protein in a pharmaceutically effective carrier or of said control mixture in the pharmaceutically effective carrier, the administration being at intervals of not less than twelve hours and not more than 72 hours between each of the doses.

7. The method of claim 6, wherein the mouse model of IDDM is the non-obese diabetic (NOD) mouse cyclophosphamide induced diabetes model.

8. The method of claim 6, wherein the mouse model of IDDM is the NOD/Severe Combined Immunodeficiency (SCID) mouse adoptive transfer diabetes model.

9. The method of claim 1, wherein the repeated administration comprises administration of at least two doses at an interval of not less than twelve hours and not more than 72 hours.

10. A method of treating a patient selected from the group consisting of patients predicted to be at risk of developing Type 1 diabetes and patients suffering from Type 1 diabetes, said method comprising the repeated administration of a dose of a measured amount of a chimeric fusion protein in a pharmaceutically effective carrier to said patient, said chimeric fusion protein comprising the amino acid sequence spanning amino acid residues 2 to 154 of SEQ ID NO:1.

11. A method of treating a patient selected from the group consisting of patients predicted to be at risk of developing Type 1 diabetes and patients suffering from Type 1 diabetes, said method comprising the repeated administration of a dose of a measured amount of a chimeric fusion protein in a pharmaceutically effective carrier to said patient, said chimeric fusion protein comprising the amino acid sequence spanning amino acid residues 2 to 174 of SEQ ID NO:2.

12. A method of treating a patient selected from the group consisting of patients predicted to be at risk of developing Type 1 diabetes and patients suffering from Type 1 diabetes, said method comprising the repeated administration of a dose of a measured amount of a chimeric fusion protein in a pharmaceutically effective carrier to said patient, said chimeric fusion protein comprising the amino acid sequence spanning amino acid residues 2 to 138 of SEQ ID NO:3.

13. A method of treating a patient selected from the group consisting of patients predicted to be at risk of developing Type 1 diabetes and patients suffering from Type 1 diabetes, said method comprising the repeated administration of a dose of a measured amount of a chimeric fusion protein in a pharmaceutically effective carrier to said patient, said chimeric fusion protein comprising the amino acid sequence spanning amino acid residues 2 to 175 of SEQ ID NO:4.

14. A method of treating a patient selected from the group consisting of patients predicted to be at risk of developing Type 1 diabetes and patients suffering from Type 1 diabetes, said method comprising the repeated administration of a dose of a measured amount of a chimeric fusion protein in a pharmaceutically effective carrier to said patient, said chimeric fusion protein comprising the amino acid sequence spanning amino acid residues 2 to 226 of SEQ ID NO:5.

15. A method of treating a patient selected from the group consisting of patients predicted to be at risk of developing Type 1 diabetes and patients suffering from Type 1 diabetes, said method comprising the repeated administration of a dose of a measured amount of a chimeric fusion protein in a pharmaceutically effective carrier to said patient, said chimeric fusion protein comprising the amino acid sequence spanning amino acid residues 2 to 387 of SEQ ID NO:6.

16. A method of treating a patient selected from the group consisting of patients predicted to be at risk of developing Type 1 diabetes and patients suffering from Type 1 diabetes, said method comprising the repeated administration of a dose of a measured amount of a chimeric fusion protein in a pharmaceutically effective carrier to said patient, said chimeric fusion protein comprising the amino acid sequence spanning amino acid residues 2 to 438 of SEQ ID NO:7.

* * * * *

SEQUENCE LISTING

<160> NUMBER OF SEQ ID NOS: 37

<210> SEQ ID NO 1
<211> LENGTH: 160
<212> TYPE: PRT
<213> ORGANISM: Artificial Sequence
<220> FEATURE:
<223> OTHER INFORMATION: IG1 fusion protein for hGAD65 (human glutamate decarboxylase)

<400> SEQUENCE: 1

```
Met Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr Arg
             20                  25                  30

Arg Glu Ala Glu Asp Leu Asn Met Tyr Ala Met Met Ile Ala Arg Phe
         35                  40                  45

Lys Met Phe Pro Glu Val Lys Glu Lys Gly Met Ala Ala Leu Pro Arg
     50                  55                  60

Leu Ile Ala Phe Thr Ser Glu Lys Cys Leu Leu Ala Glu Tyr Leu
65                  70                  75                  80

Tyr Asn Ile Ile Lys Asn Arg Glu Gly Tyr Glu Met Val Phe Asp Gly
                 85                  90                  95

Lys Pro Gln His Thr Asn Val Cys Phe Trp Tyr Ile Pro Pro Ser Leu
            100                 105                 110

Arg Thr Leu Glu Asp Asn Glu Glu Arg Met Ser Arg Leu Ser Lys Val
        115                 120                 125

Ala Pro Val Ile Lys Ala Arg Met Met Glu Tyr Gly Thr Thr Met Val
    130                 135                 140

Ser Tyr Gln Pro Leu Gly Asp Lys Val Asn His His His His His His
145                 150                 155                 160
```

<210> SEQ ID NO 2
<211> LENGTH: 180
<212> TYPE: PRT
<213> ORGANISM: Artificial Sequence
<220> FEATURE:
<223> OTHER INFORMATION: IG2 fusion protein for hGAD65 (human glutamate decarboxylase)

<400> SEQUENCE: 2

```
Met Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr Arg
             20                  25                  30

Arg Glu Ala Glu Asp Leu Met Asn Ile Leu Leu Gln Tyr Val Val Lys
         35                  40                  45

Ser Phe Asp Asn Met Tyr Ala Met Met Ile Ala Arg Phe Lys Met Phe
     50                  55                  60

Pro Glu Val Lys Glu Lys Gly Met Ala Ala Leu Pro Arg Leu Ile Ala
65                  70                  75                  80

Phe Thr Ser Glu His Ser His Phe Ser Leu Lys Lys Cys Leu Glu Leu
                 85                  90                  95

Ala Glu Tyr Leu Tyr Asn Ile Ile Lys Asn Arg Glu Gly Tyr Glu Met
            100                 105                 110

Val Phe Asp Gly Lys Pro Gln His Thr Asn Val Cys Phe Trp Tyr Ile
        115                 120                 125
```

```
Pro Pro Ser Leu Arg Thr Leu Glu Asp Asn Glu Glu Arg Met Ser Arg
        130                 135                 140

Leu Ser Lys Val Ala Pro Val Ile Lys Ala Arg Met Met Glu Tyr Gly
145                 150                 155                 160

Thr Thr Met Val Ser Tyr Gln Pro Leu Gly Asp Lys Val Asn His His
                165                 170                 175

His His His His
        180

<210> SEQ ID NO 3
<211> LENGTH: 144
<212> TYPE: PRT
<213> ORGANISM: Artificial Sequence
<220> FEATURE:
<223> OTHER INFORMATION: IG3 fusion protein for hGAD65 (human glutamate
      decarboxylase)

<400> SEQUENCE: 3

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Met Asn Ile Leu Leu Gln Tyr Val Val Lys
        35                  40                  45

Ser Phe Asp Asn Met Tyr Ala Met Met Ile Ala Arg Phe Lys Met Phe
    50                  55                  60

Pro Glu Val Lys Glu Lys Gly Met Ala Ala Leu Pro Arg Leu Ile Ala
65                  70                  75                  80

Phe Thr Ser Glu His Ser His Phe Ser Leu Lys Lys Cys Leu Glu Leu
                85                  90                  95

Ala Glu Tyr Leu Tyr Asn Ile Ile Lys Asn Arg Glu Gly Tyr Glu Met
            100                 105                 110

Val Phe Asp Gly Lys Pro Gln His Thr Asn Val Cys Phe Trp Tyr Ile
        115                 120                 125

Pro Pro Ser Leu Arg Thr Leu Glu Asp Asn His His His His His His
    130                 135                 140

<210> SEQ ID NO 4
<211> LENGTH: 181
<212> TYPE: PRT
<213> ORGANISM: Artificial Sequence
<220> FEATURE:
<223> OTHER INFORMATION: IG4 fusion protein for hGAD65 (human glutamate
      decarboxylase)

<400> SEQUENCE: 4

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
    50                  55                  60

Lys Arg Gly Thr Asn Met Phe Thr Tyr Glu Ile Ala Pro Val Phe Val
65                  70                  75                  80

Leu Leu Glu Tyr Val Thr Leu Lys Lys Met Arg Glu Ile Ile Gly Trp
                85                  90                  95
```

```
Pro Gly Gly Ser Gly Asp Gly Gly Met Asn Ile Leu Leu Gln Tyr
            100                 105                 110

Val Val Lys Ser Phe Asp Asn Met Tyr Ala Met Met Ile Ala Arg Phe
            115                 120                 125

Lys Met Phe Pro Glu Val Lys Glu Lys Gly Met Ala Ala Leu Pro Arg
130                 135                 140

Leu Gly Gly Gly Ile Ala Phe Thr Ser Glu His Ser His Phe Ser Leu
145                 150                 155                 160

Lys Lys Gly Ala Ala Ala Leu Gly Ile Gly Thr Asp Ser Val Ile His
                165                 170                 175

His His His His His
            180

<210> SEQ ID NO 5
<211> LENGTH: 232
<212> TYPE: PRT
<213> ORGANISM: Artificial Sequence
<220> FEATURE:
<223> OTHER INFORMATION: IG5 fusion protein for hGAD65 (human glutamate
      decarboxylase)

<400> SEQUENCE: 5

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
            35                  40                  45

Pro Gly Ala Gly Ser Leu Gln Pro Leu Ala Leu Glu Gly Ser Leu Gln
50                  55                  60

Lys Arg Gly Thr Asn Met Phe Thr Tyr Glu Ile Ala Pro Val Phe Val
65                  70                  75                  80

Leu Leu Glu Tyr Val Thr Leu Lys Lys Met Arg Glu Ile Ile Gly Trp
            85                  90                  95

Pro Gly Gly Ser Gly Asp Gly Gly Met Asn Ile Leu Leu Gln Tyr
            100                 105                 110

Val Val Lys Ser Phe Asp Asn Met Tyr Ala Met Met Ile Ala Arg Phe
            115                 120                 125

Lys Met Phe Pro Glu Val Lys Glu Lys Gly Met Ala Ala Leu Pro Arg
130                 135                 140

Leu Gly Gly Gly Ile Ala Phe Thr Ser Glu His Ser His Phe Ser Leu
145                 150                 155                 160

Lys Lys Gly Ala Ala Ala Leu Gly Ile Gly Thr Asp Ser Val Ile Gly
                165                 170                 175

Gly Gly Tyr Ile Pro Pro Ser Leu Arg Thr Leu Glu Asp Asn Glu Glu
            180                 185                 190

Arg Met Ser Arg Leu Ser Lys Val Ala Pro Val Ile Lys Ala Arg Met
            195                 200                 205

Met Glu Tyr Gly Thr Thr Met Val Ser Tyr Gln Pro Leu Gly Asp Lys
            210                 215                 220

Val Asn His His His His His His
225                 230

<210> SEQ ID NO 6
<211> LENGTH: 393
<212> TYPE: PRT
```

<213> ORGANISM: Artificial Sequence
<220> FEATURE:
<223> OTHER INFORMATION: IG6 fusion protein for hGAD65 (human glutamate decarboxylase)

<400> SEQUENCE: 6

```
Met Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr Arg
             20                  25                  30

Arg Glu Ala Glu Asp Leu Gln Val Gly Gln Val Glu Leu Gly Gly Gly
         35                  40                  45

Pro Gly Ala Gly Ser Leu Gln Pro Leu Ala Leu Glu Gly Ser Leu Gln
 50                  55                  60

Lys Arg Gly Thr Asn Met Phe Thr Tyr Glu Ile Ala Pro Val Phe Val
 65                  70                  75                  80

Leu Leu Glu Tyr Val Thr Leu Lys Lys Met Arg Glu Ile Ile Gly Trp
                 85                  90                  95

Pro Gly Gly Ser Gly Asp Gly Gly Met Asn Ile Leu Leu Gln Tyr
            100                 105                 110

Val Val Lys Ser Phe Asp Asn Met Tyr Ala Met Met Ile Ala Arg Phe
            115                 120                 125

Lys Met Phe Pro Glu Val Lys Glu Lys Gly Met Ala Ala Leu Pro Arg
        130                 135                 140

Leu Gly Gly Gly Ile Ala Phe Thr Ser Glu His Ser His Phe Ser Leu
145                 150                 155                 160

Lys Lys Gly Ala Ala Ala Leu Gly Ile Gly Thr Asp Ser Val Ile Gly
                165                 170                 175

Gly Gly Ile Glu His Asp Pro Arg Met Pro Ala Tyr Ile Ala Thr Gln
            180                 185                 190

Gly Pro Leu Ser His Thr Ile Ala Asp Phe Trp Gln Met Val Trp Glu
        195                 200                 205

Ser Gly Cys Thr Val Ile Val Met Leu Thr Pro Leu Val Glu Asp Gly
210                 215                 220

Val Lys Gln Cys Asp Arg Tyr Trp Pro Asp Glu Gly Ala Ser Leu Tyr
225                 230                 235                 240

His Val Tyr Glu Val Asn Leu Val Ser Glu His Ile Trp Cys Glu Asp
                245                 250                 255

Phe Leu Val Arg Ser Phe Tyr Leu Lys Asn Val Gln Thr Gln Glu Thr
            260                 265                 270

Arg Thr Leu Thr Gln Phe His Phe Leu Ser Trp Pro Ala Glu Gly Thr
        275                 280                 285

Pro Ala Ser Thr Arg Pro Leu Leu Asp Phe Arg Arg Lys Val Asn Lys
290                 295                 300

Cys Tyr Arg Gly Arg Ser Cys Pro Ile Ile Val His Cys Ser Asp Gly
305                 310                 315                 320

Ala Gly Arg Thr Gly Thr Tyr Ile Leu Ile Asp Met Val Leu Asn Arg
                325                 330                 335

Met Ala Lys Gly Val Lys Glu Ile Asp Ile Ala Ala Thr Leu Glu His
            340                 345                 350

Val Arg Asp Gln Arg Pro Gly Leu Val Arg Ser Lys Asp Gln Phe Glu
        355                 360                 365

Phe Ala Leu Thr Ala Val Ala Glu Glu Val Asn Ala Ile Leu Lys Ala
370                 375                 380
```

Leu Pro Gln His His His His His His
385                 390

<210> SEQ ID NO 7
<211> LENGTH: 444
<212> TYPE: PRT
<213> ORGANISM: Artificial Sequence
<220> FEATURE:
<223> OTHER INFORMATION: IG7 fusion protein for hGAD65 (human glutamate
      decarboxylase)

<400> SEQUENCE: 7

Met Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
 50                  55                  60

Lys Arg Gly Thr Asn Met Phe Thr Tyr Glu Ile Ala Pro Val Phe Val
 65                  70                  75                  80

Leu Leu Glu Tyr Val Thr Leu Lys Lys Met Arg Glu Ile Ile Gly Trp
                85                  90                  95

Pro Gly Gly Ser Gly Asp Gly Gly Met Asn Ile Leu Leu Gln Tyr
            100                 105                 110

Val Val Lys Ser Phe Asp Asn Met Tyr Ala Met Met Ile Ala Arg Phe
            115                 120                 125

Lys Met Phe Pro Glu Val Lys Glu Lys Gly Met Ala Ala Leu Pro Arg
130                 135                 140

Leu Gly Gly Gly Ile Ala Phe Thr Ser Glu His Ser His Phe Ser Leu
145                 150                 155                 160

Lys Lys Gly Ala Ala Ala Leu Gly Ile Gly Thr Asp Ser Val Ile Gly
                165                 170                 175

Gly Gly Tyr Ile Pro Pro Ser Leu Arg Thr Leu Glu Asp Asn Glu Glu
            180                 185                 190

Arg Met Ser Arg Leu Ser Lys Val Ala Pro Val Ile Lys Ala Arg Met
        195                 200                 205

Met Glu Tyr Gly Thr Thr Met Val Ser Tyr Gln Pro Leu Gly Asp Lys
210                 215                 220

Val Asn Gly Gly Gly Ile Glu His Asp Pro Arg Met Pro Ala Tyr Ile
225                 230                 235                 240

Ala Thr Gln Gly Pro Leu Ser His Thr Ile Ala Asp Phe Trp Gln Met
                245                 250                 255

Val Trp Glu Ser Gly Cys Thr Val Ile Val Met Leu Thr Pro Leu Val
            260                 265                 270

Glu Asp Gly Val Lys Gln Cys Asp Arg Tyr Trp Pro Asp Glu Gly Ala
        275                 280                 285

Ser Leu Tyr His Val Tyr Glu Val Asn Leu Val Ser Glu His Ile Trp
290                 295                 300

Cys Glu Asp Phe Leu Val Arg Ser Phe Tyr Leu Lys Asn Val Gln Thr
305                 310                 315                 320

Gln Glu Thr Arg Thr Leu Thr Gln Phe His Phe Leu Ser Trp Pro Ala
                325                 330                 335

Glu Gly Thr Pro Ala Ser Thr Arg Pro Leu Leu Asp Phe Arg Arg Lys
            340                 345                 350

```
Val Asn Lys Cys Tyr Arg Gly Arg Ser Cys Pro Ile Ile Val His Cys
        355                 360                 365

Ser Asp Gly Ala Gly Arg Thr Gly Thr Tyr Ile Leu Ile Asp Met Val
        370                 375                 380

Leu Asn Arg Met Ala Lys Gly Val Lys Glu Ile Asp Ile Ala Ala Thr
385                 390                 395                 400

Leu Glu His Val Arg Asp Gln Arg Pro Gly Leu Val Arg Ser Lys Asp
                405                 410                 415

Gln Phe Glu Phe Ala Leu Thr Ala Val Ala Glu Glu Val Asn Ala Ile
                420                 425                 430

Leu Lys Ala Leu Pro Gln His His His His His
        435                 440

<210> SEQ ID NO 8
<211> LENGTH: 173
<212> TYPE: PRT
<213> ORGANISM: Artificial Sequence
<220> FEATURE:
<223> OTHER INFORMATION: IG4NHB hypothetical fusion protein

<400> SEQUENCE: 8

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
    50                  55                  60

Lys Arg Gly Met Asn Ile Leu Leu Gln Tyr Val Val Lys Ser Phe Asp
65                  70                  75                  80

Asn Met Tyr Ala Met Met Ile Ala Arg Phe Lys Met Phe Pro Glu Val
                85                  90                  95

Lys Glu Lys Gly Met Ala Ala Leu Pro Arg Leu Ile Ala Phe Thr Ser
            100                 105                 110

Glu His Ser His Phe Ser Leu Lys Lys Cys Leu Glu Leu Ala Glu Tyr
        115                 120                 125

Leu Tyr Asn Ile Ile Lys Asn Arg Glu Gly Tyr Glu Met Val Phe Asp
    130                 135                 140

Gly Lys Pro Gln His Thr Asn Val Cys Phe Trp Tyr Ile Pro Pro Ser
145                 150                 155                 160

Leu Arg Thr Leu Glu Asp Asn His His His His His
                165                 170

<210> SEQ ID NO 9
<211> LENGTH: 3
<212> TYPE: PRT
<213> ORGANISM: Artificial Sequence
<220> FEATURE:
<223> OTHER INFORMATION: helix breaker

<400> SEQUENCE: 9

Pro Pro Pro
 1

<210> SEQ ID NO 10
<211> LENGTH: 3
<212> TYPE: PRT
```

<213> ORGANISM: Artificial Sequence
<220> FEATURE:
<223> OTHER INFORMATION: helix breaker

<400> SEQUENCE: 10

Gly Gly Gly
 1

<210> SEQ ID NO 11
<211> LENGTH: 139
<212> TYPE: DNA
<213> ORGANISM: Artificial Sequence
<220> FEATURE:
<223> OTHER INFORMATION: prIG1 primer

<400> SEQUENCE: 11
catatgttcg ttaaccagca tctgtgtggc tctcacctgg ttgaagccct gtatctggtt      60
tgcggtgaac gcggcttttt ctacaccccg aaaaccgtc gtgaagcgga agatctgaac      120
atgtatgcca tgatgatcg                                                  139

<210> SEQ ID NO 12
<211> LENGTH: 143
<212> TYPE: DNA
<213> ORGANISM: Artificial Sequence
<220> FEATURE:
<223> OTHER INFORMATION: prIG2 primer

<400> SEQUENCE: 12
ggtttttaat gatgttgtac agatattccg ccagttccag acatttttca gaggtaaagg      60
caatcagacg cggcagcgcg gccataccct tttctttaac ttccgggaac attttaaagc     120
gcgcgatcat catggcatac atg                                             143

<210> SEQ ID NO 13
<211> LENGTH: 138
<212> TYPE: DNA
<213> ORGANISM: Artificial Sequence
<220> FEATURE:
<223> OTHER INFORMATION: prIG3 primer

<400> SEQUENCE: 13
gtacaacatc attaaaaacc gcgaaggcta tgaaatggtt ttcgatggta aaccgcagca      60
taccaacgtt tgcttttggt acatcccgcc gagcctgcgt accctggaag ataacgaaga    120
acgcatgagc cgtctgtc                                                   138

<210> SEQ ID NO 14
<211> LENGTH: 132
<212> TYPE: DNA
<213> ORGANISM: Artificial Sequence
<220> FEATURE:
<223> OTHER INFORMATION: prIG4 primer

<400> SEQUENCE: 14
ggatccttaa tggtgatggt gatggtggtt aactttatca cccagcggct ggtagctaac      60
catggtggtg ccatattcca tcatgcgcgc tttaataacc ggggcaactt tagacagacg     120
gctcatgcgt tc                                                         132

<210> SEQ ID NO 15
<211> LENGTH: 18
<212> TYPE: DNA
<213> ORGANISM: Artificial Sequence
<220> FEATURE:

<223> OTHER INFORMATION: prIG5 primer

<400> SEQUENCE: 15
catatgttcg ttaaccag                                                   18

<210> SEQ ID NO 16
<211> LENGTH: 18
<212> TYPE: DNA
<213> ORGANISM: Artificial Sequence
<220> FEATURE:
<223> OTHER INFORMATION: prIGG primer

<400> SEQUENCE: 16
ggatccttaa tggtgatg                                                   18

<210> SEQ ID NO 17
<211> LENGTH: 492
<212> TYPE: DNA
<213> ORGANISM: Artificial Sequence
<220> FEATURE:
<223> OTHER INFORMATION: IG1 fusion protein coding sequence for hGAD65
      (human glutamate decarboxylase)

<400> SEQUENCE: 17
catatgttcg ttaaccagca tctgtgtggc tctcacctgg ttgaagccct gtatctggtt     60
tgcggtgaac gcggctttt ctacacccccg aaaacccgtc gtgaagcgga agatctgaac   120
atgtatgcca tgatgatcgc gcgctttaaa atgttcccgg aagttaaaga aaaaggtatg   180
gccgcgctgc gccgtctgat tgcctttacc tctgaaaaat gtctggaact ggcggaatat   240
ctgtacaaca tcattaaaaa ccgcgaaggc tatgaaatgg ttttcgatgg taaaccgcag   300
cataccaacg tttgcttttg gtacatcccg ccgagcctgc gtaccctgga agataacgaa   360
gaacgcatga gccgtctgtc taaagttgcc ccggttatta agcgcgcat gatggaatat   420 ggcaccacca tggttagcta ccagccgctg ggtgataaag ttaaccacca tcaccatcac   480
cattaaggat cc                                                        492

<210> SEQ ID NO 18
<211> LENGTH: 64
<212> TYPE: DNA
<213> ORGANISM: Artificial Sequence
<220> FEATURE:
<223> OTHER INFORMATION: prIG7 primer

<400> SEQUENCE: 18
agatctgatg aacattctgc tgcagtatgt tgttaaaagc ttcgataaca tgtatgccat     60
gatg                                                                 64

<210> SEQ ID NO 19
<211> LENGTH: 78
<212> TYPE: DNA
<213> ORGANISM: Artificial Sequence
<220> FEATURE:
<223> OTHER INFORMATION: prIG8 primer

<400> SEQUENCE: 19
tgtacagata ttccgccagt tccagacatt ttttcagaga aaatggcta tgttcagagg     60 taaaggcaat cagacgcg                                                  78

<210> SEQ ID NO 20
<211> LENGTH: 27
<212> TYPE: DNA

<213> ORGANISM: Artificial Sequence
<220> FEATURE:
<223> OTHER INFORMATION: prIG12 primer

<400> SEQUENCE: 20
tgtacagata ttccgccagt tccagac                                         27

<210> SEQ ID NO 21
<211> LENGTH: 552
<212> TYPE: DNA
<213> ORGANISM: Artificial Sequence
<220> FEATURE:
<223> OTHER INFORMATION: IG2 fusion protein coding sequence for hGAD65
      (human glutamate decarboxylase)

<400> SEQUENCE: 21
catatgttcg ttaaccagca tctgtgtggc tctcacctgg ttgaagccct gtatctggtt      60
tgcggtgaac gcggctttt ctacaccccg aaaacccgtc gtgaagcgga agatctgatg     120
aacattctgc tgcagtatgt tgttaaaagc ttcgataaca tgtatgccat gatgatcgcg     180
cgctttaaaa tgttcccgga agttaaagaa aaaggtatgg ccgcgctgcc gcgtctgatt     240
gcctttacct ctgaacatag ccattttct ctgaaaaat gtctggaact ggcggaatat      300
ctgtacaaca tcattaaaaa ccgcgaaggc tatgaaatgg ttttcgatgg taaaccgcag     360
cataccaacg tttgcttttg gtacatcccg ccgagcctgc gtaccctgga agataacgaa     420
gaacgcatga ccgtctgtc taaagttgcc ccggttatta agcgcgcat gatgaatat       480 ggcaccacca tggttagcta ccagccgctg ggtgataaag ttaaccacca tcaccatcac     540
cattaaggat cc                                                        552

<210> SEQ ID NO 22
<211> LENGTH: 46
<212> TYPE: DNA
<213> ORGANISM: Artificial Sequence
<220> FEATURE:
<223> OTHER INFORMATION: prIG13 primer

<400> SEQUENCE: 22
ggatccttaa atggtgatgg tgatggtggt tatcttccag ggtacg                    46

<210> SEQ ID NO 23
<211> LENGTH: 444
<212> TYPE: DNA
<213> ORGANISM: Artificial Sequence
<220> FEATURE:
<223> OTHER INFORMATION: IG3 fusion protein coding sequence for hGAD65
      (human glutamate decarboxylase)

<400> SEQUENCE: 23
catatgttcg ttaaccagca tctgtgtggc tctcacctgg ttgaagccct gtatctggtt      60
tgcggtgaac gcggctttt ctacaccccg aaaacccgtc gtgaagcgga agatctgatg     120
aacattctgc tgcagtatgt tgttaaaagc ttcgataaca tgtatgccat gatgatcgcg     180
cgctttaaaa tgttcccgga agttaaagaa aaaggtatgg ccgcgctgcc gcgtctgatt     240
gcctttacct ctgaacatag ccattttct ctgaaaaat gtctggaact ggcggaatat      300
ctgtacaaca tcattaaaaa ccgcgaaggc tatgaaatgg ttttcgatgg taaaccgcag     360
cataccaacg tttgcttttg gtacatcccg ccgagcctgc gtaccctgga agataaccac     420
catcaccatc accattaagg atcc                                           444

<210> SEQ ID NO 24
<211> LENGTH: 555
<212> TYPE: DNA
<213> ORGANISM: Artificial Sequence
<220> FEATURE:
<223> OTHER INFORMATION: IG4 fusion protein coding sequence for hGAD65
      (human glutamate decarboxylase)

<400> SEQUENCE: 24

```
catatgttcg ttaaccagca tctgtgtggc tctcacctgg ttgaagccct gtatctggtt      60
tgcggtgaac gcggctttt ctacaccccg aaaacccgtc gtgaagcgga agatctgcag     120
gtggggcagg tggagctggg cggggccct ggtgcaggca gcctgcagcc cttggccctg     180
gaggggtccc tgcagaagcg tggcactaac atgttcacct atgaaattgc tccagtattt    240
gtgcttttgg aatatgtcac actaaagaaa atgagagaaa tcattggctg gccagggggc    300
tctggcgatg gaggcggtat gaacattctg ctgcagtatg ttgttaaaag cttcgataac    360
atgtatgcca tgatgatcgc gcgctttaaa atgttcccgg aagttaaaga aaaaggtatg    420
gccgcgctgc cgcgtctggg aggcggtatt gcctttacct ctgaacatag ccattttctt    480
ctgaaaaaag gagctgcagc cttagggatt ggaacagaca gcgtgattca ccatcaccat    540
caccattaag gatcc                                                     555
```

<210> SEQ ID NO 25
<211> LENGTH: 24
<212> TYPE: DNA
<213> ORGANISM: Artificial Sequence
<220> FEATURE:
<223> OTHER INFORMATION: prIG14 primer

<400> SEQUENCE: 25

```
catatgttcg ttaaccagca tctg                                            24
```

<210> SEQ ID NO 26
<211> LENGTH: 69
<212> TYPE: DNA
<213> ORGANISM: Artificial Sequence
<220> FEATURE:
<223> OTHER INFORMATION: prIG15 primer

<400> SEQUENCE: 26

```
gctgcctgca ccagggcccc cgcccagctc cacctgcccc acctgcagat cttccgcttc     60
acgacgggt                                                             69
```

<210> SEQ ID NO 27
<211> LENGTH: 66
<212> TYPE: DNA
<213> ORGANISM: Artificial Sequence
<220> FEATURE:
<223> OTHER INFORMATION: prIG16 primer

<400> SEQUENCE: 27

```
agtgccacgc ttctgcaggg acccctccag ggccaagggc tgcaggctgc ctgcaccagg     60
gccccc                                                                66
```

<210> SEQ ID NO 28
<211> LENGTH: 69
<212> TYPE: DNA
<213> ORGANISM: Artificial Sequence
<220> FEATURE:
<223> OTHER INFORMATION: prIG17 primer

<400> SEQUENCE: 28

```
ttccaaaagc acaaatactg gagcaatttc ataggtgaac atgttagtgc cacgcttctg    60
cagggaccc                                                            69

<210> SEQ ID NO 29
<211> LENGTH: 69
<212> TYPE: DNA
<213> ORGANISM: Artificial Sequence
<220> FEATURE:
<223> OTHER INFORMATION: prIG18 primer

<400> SEQUENCE: 29
ccctggccag ccaatgattt ctctcatttt ctttagtgtg acatattcca aaagcacaaa    60
tactggagc                                                            69

<210> SEQ ID NO 30
<211> LENGTH: 69
<212> TYPE: DNA
<213> ORGANISM: Artificial Sequence
<220> FEATURE:
<223> OTHER INFORMATION: prIG19 primer

<400> SEQUENCE: 30
agagaaatca ttggctggcc aggggctct ggcgatggag gcggtatgaa cattctgctg     60
cagtatgtt                                                            69

<210> SEQ ID NO 31
<211> LENGTH: 68
<212> TYPE: DNA
<213> ORGANISM: Artificial Sequence
<220> FEATURE:
<223> OTHER INFORMATION: prIG20 primer

<400> SEQUENCE: 31
cagagaaaaa tggctatgtt cagaggtaaa ggcaataccg cctcccagac gcggcagcgc    60
ggccatac                                                             68

<210> SEQ ID NO 32
<211> LENGTH: 69
<212> TYPE: DNA
<213> ORGANISM: Artificial Sequence
<220> FEATURE:
<223> OTHER INFORMATION: prIG21 primer

<400> SEQUENCE: 32
aatcacgctg tctgttccaa tccctaaggc tgcagctcct tttttcagag aaaaatggct    60
atgttcaga                                                            69

<210> SEQ ID NO 33
<211> LENGTH: 60
<212> TYPE: DNA
<213> ORGANISM: Artificial Sequence
<220> FEATURE:
<223> OTHER INFORMATION: prIG22 primer

<400> SEQUENCE: 33
ttagggattg aacagacag cgtgattgga ggcggttaca tcccgccgag cctgcgtacc    60

<210> SEQ ID NO 34
<211> LENGTH: 24
<212> TYPE: DNA
<213> ORGANISM: Artificial Sequence
<220> FEATURE:
```

<223> OTHER INFORMATION: prIG23 primer

<400> SEQUENCE: 34
ggatccttaa tggtgatggt gatg                                              24

<210> SEQ ID NO 35
<211> LENGTH: 708
<212> TYPE: DNA
<213> ORGANISM: Artificial Sequence
<220> FEATURE:
<223> OTHER INFORMATION: IG5 fusion protein coding sequence for hGAD65
      (human glutamate decarboxylase)

<400> SEQUENCE: 35

| | | | |
|---|---|---|---|
| catatgttcg ttaaccagca tctgtgtggc tctcacctgg ttgaagccct gtatctggtt | | | 60 |
| tgcggtgaac gcggctttt ctacaccccg aaaacccgtc gtgaagcgga agatctgcag | | | 120 |
| gtggggcagg tggagctggg cggggccct ggtgcaggca gcctgcagcc cttggccctg | | | 180 |
| gagggtccc tgcagaagcg tggcactaac atgttcacct atgaaattgc tccagtattt | | | 240 |
| gtgcttttgg aatatgtcac actaaagaaa atgagagaaa tcattggctg ccagggggc | | | 300 |
| tctggcgatg gaggcggtat gaacattctg ctgcagtatg ttgttaaaag cttcgataac | | | 360 |
| atgtatgcca tgatgatcgc gcgctttaaa atgttcccgg aagttaaaga aaaaggtatg | | | 420 |
| gccgcgctgc cgcgtctggg aggcggtatt gcctttacct ctgaacatag ccattttct | | | 480 |
| ctgaaaaaag gagctgcagc cttagggatt ggaacagaca gcgtgattgg aggcggttac | | | 540 |
| attcctccaa gcttgcgtac tctggaagac aatgaagaac gcatgagccg tctgtctaaa | | | 600 |
| gttgccccgg ttattaaagc gcgcatgatg gaatatggca ccaccatggt tagctaccag | | | 660 |
| ccgctgggtg ataaagttaa ccaccatcac catcaccatt aaggatcc | | | 708 |

<210> SEQ ID NO 36
<211> LENGTH: 1191
<212> TYPE: DNA
<213> ORGANISM: Artificial Sequence
<220> FEATURE:
<223> OTHER INFORMATION: IG6 fusion protein coding sequence for hGAD65
      (human glutamate decarboxylase)

<400> SEQUENCE: 36

| | | | |
|---|---|---|---|
| catatgttcg ttaaccagca tctgtgtggc tctcacctgg ttgaagccct gtatctggtt | | | 60 |
| tgcggtgaac gcggctttt ctacaccccg aaaacccgtc gtgaagcgga agatctgcag | | | 120 |
| gtggggcagg tggagctggg cggggccct ggtgcaggca gcctgcagcc cttggccctg | | | 180 |
| gagggtccc tgcagaagcg tggcactaac atgttcacct atgaaattgc tccagtattt | | | 240 |
| gtgcttttgg aatatgtcac actaaagaaa atgagagaaa tcattggctg ccagggggc | | | 300 |
| tctggcgatg gaggcggtat gaacattctg ctgcagtatg ttgttaaaag cttcgataac | | | 360 |
| atgtatgcca tgatgatcgc gcgctttaaa atgttcccgg aagttaaaga aaaaggtatg | | | 420 |
| gccgcgctgc cgcgtctggg aggcggtatt gcctttacct ctgaacatag ccattttct | | | 480 |
| ctgaaaaaag gagctgcagc cttagggatt ggaacagaca gcgtgattgg aggcggtatt | | | 540 |
| gagcatgacc ctcggatgcc agcctacata gccacgcagg gcccgctgtc ccataccatc | | | 600 |
| gcagacttct ggcagatggt gtgggagagc ggctgcaccg tcatcgtcat gctgaccccg | | | 660 |
| ctggtggagg atggtgtcaa gcagtgtgac cgctactggc cagatgaggg tgcctccctc | | | 720 |
| taccacgtat atgaggtgaa cctggtgtcg gagcacatct ggtgcgagga ctttctggtg | | | 780 |
| cggagcttct acctgaagaa cgtgcagacc caggagacgc gcacgctcac gcagttccac | | | 840 |

-continued

```
ttcctcagct ggccggcaga gggcacaccg gcctccacgc ggcccctgct ggacttccgc      900
aggaaggtga acaagtgcta ccggggccgc tcctgcccca tcatcgtgca ctgcagtgat      960
ggtgcgggga ggaccggcac ctacatcctc atcgacatgg tcctgaaccg catggcaaaa     1020
ggagtgaagg agattgacat cgctgccacc ctggagcatg tccgtgacca gcggcctggc     1080
cttgtccgct ctaaggacca gtttgaattt gccctgacag ccgtggcgga ggaagtgaat     1140
gccatcctca aggccctgcc ccagcaccat caccatcacc attaaggatc c              1191
```

<210> SEQ ID NO 37
<211> LENGTH: 1344
<212> TYPE: DNA
<213> ORGANISM: Artificial Sequence
<220> FEATURE:
<223> OTHER INFORMATION: IG7 fusion protein coding sequence for hGAD65
      (human glutamate decarboxylase)

<400> SEQUENCE: 37

```
catatgttcg ttaaccagca tctgtgtggc tctcacctgg ttgaagccct gtatctggtt       60
tgcggtgaac gcggcttttt ctacaccccg aaaacccgtc gtgaagcgga agatctgcag      120
gtggggcagg tggagctggg cggggggccct ggtgcaggca gcctgcagcc cttggccctg     180
gaggggtccc tgcagaagcg tggcactaac atgttcacct atgaaattgc tccagtattt     240
gtgcttttgg aatatgtcac actaaagaaa atgagagaaa tcattggctg ccagggggc      300 tctggcgatg gaggcggtat gaacattctg ctgcagtatg ttgttaaaag cttcgataac     360
atgtatgcca tgatgatcgc gcgctttaaa atgttcccgg aagttaaaga aaaaggtatg     420
gccgcgctgc cgcgtctggg aggcggtatt gcctttacct ctgaacatag ccattttctct    480 ctgaaaaaag gagctgcagc cttagggatt ggaacagaca gcgtgattgg aggcggttac     540
attcctccaa gcttgcgtac tctggaagac aatgaagaac gcatgagccg tctgtctaaa     600
gttgccccgg ttattaaagc gcgcatgatg gaatatggca ccaccatggt tagctaccag     660
ccgctgggtg ataaagttaa cggaggcggt attgagcatg accctcggat gccagcctac     720
atagccacgc agggcccgct gtcccatacc atcgcagact ctggcagat  ggtgtgggag     780 agcggctgca ccgtcatcgt catgctgacc ccgctggtgg aggatggtgt caagcagtgt     840
gaccgctact ggccagatga gggtgcctcc ctctaccacg tatatgaggt gaacctggtg     900
tcggagcaca tctggtgcga ggactttctg gtgcggagct tctacctgaa gaacgtgcag     960
acccaggaga cgcgcacgct cacgcagttc cacttcctca gctggccggc agagggcaca    1020
ccggcctcca gcggcccct gctggacttc gcaggaagg tgaacaagtg ctaccggggc      1080
cgctcctgcc ccatcatcgt gcactgcagt gatggtgcgg ggaggaccgg cacctacatc    1140
ctcatcgaca tggtcctgaa ccgcatggca aaaggagtga aggagattga catcgctgcc    1200
accctggagc atgtccgtga ccagcggcct ggccttgtcc gctctaagga ccagtttgaa    1260
tttgccctga cagccgtggc ggaggaagtg aatgccatcc tcaaggccct gccccagcac    1320
catcaccatc accattaagg atcc                                           1344
```